(12) United States Patent
Miyamura et al.

(10) Patent No.: US 8,354,059 B2
(45) Date of Patent: Jan. 15, 2013

(54) CELL ANALYSIS CARTRIDGE

(75) Inventors: Kazuhiro Miyamura, Kyoto (JP);
Kazutaka Okamoto, Kyoto (JP)

(73) Assignee: HORIBA, Ltd., Kyoto-shi (JP)

( * ) Notice: Subject to any disclaimer, the term of this patent is extended or adjusted under 35 U.S.C. 154(b) by 0 days.

(21) Appl. No.: 13/216,115

(22) Filed: Aug. 23, 2011

(65) Prior Publication Data
US 2012/0043202 A1     Feb. 23, 2012

(30) Foreign Application Priority Data

Aug. 23, 2010  (JP) .................................. 2010-186252
Aug. 23, 2010  (JP) .................................. 2010-186258

(51) Int. Cl.
*G01N 27/00*   (2006.01)
*G01N 27/403*  (2006.01)

(52) U.S. Cl. ................................................ 422/82.02
(58) Field of Classification Search .... 422/82.01–82.03; 204/409–412, 403.01; 205/777.5
See application file for complete search history.

(56) References Cited

FOREIGN PATENT DOCUMENTS
EP      0282840 A2 *   9/1988
JP      2004-257768 A   9/2004

* cited by examiner

*Primary Examiner* — Alex Noguerola
(74) *Attorney, Agent, or Firm* — Alleman Hall McCoy Russell & Tuttle LLP

(57) ABSTRACT

Not only a downsized cartridge but also an aperture constituted simply and at low cost using a downsized configuration of the cartridge is provided. A measurement channel includes a front-surface-side channel unit provided on a front surface of a cartridge main body; a rear-surface-side channel unit provided on a rear surface of the cartridge main body; and a connection channel unit connecting the front-surface-side channel unit to the rear-surface-side channel unit. An aperture is formed in the connection channel unit, a fluid contact unit of one electrode is arranged in the front-surface-side channel unit, and a fluid contact unit of the other electrode is arranged in the rear-surface-side channel unit.

3 Claims, 18 Drawing Sheets

CELL ANALYSIS CARTRIDGE

TECHNICAL FIELD

The present invention relates to a cell analysis cartridge that analyzes a body fluid such as blood and particularly relates to a cell analysis cartridge that can be made compact in size.

BACKGROUND ART

As a cell analysis cartridge of this type, there is known a cartridge detachably attached to a micro-blood-cell-counter main body as disclosed in Patent Literature 1. The cartridge disclosed in the Patent Literature 1 includes a measurement channel circulating a diluted sample blood that is a fluid sample, an aperture provided on the measurement channel, and a pair of electrodes having fluid-contact units arranged at positions across the aperture held between the fluid-contact portions, respectively. The cartridge is used to perform a blood analysis based on an impedance change between the electrodes caused by passing of such cells as blood cells through the aperture.

Specifically, the measurement channel and the aperture are configured such that the measurement channel is provided in a plane direction of a resin substrate such as a PMMA substrate and the aperture is provided halfway along the measurement channel.

However, with the configuration of providing the measurement channel only in the plane direction, the cartridge is made larger in a plane size if the measurement channel is longer. Furthermore, there is a limit to making compact the plane size of the cartridge because of arrangement of the fluid-contact units of the paired electrodes in the plane direction across the aperture held between the fluid-contact units. In this way, the cartridge having the conventional configuration has a problem that it is difficult to meet market needs of the compact size.

Moreover, the measurement channel including the aperture is configured by forming a groove on a surface of the resin substrate by microfabrication such as micromachining. The aperture, in particular, needs to be formed with high precision because a size of the aperture is appropriately set according to a size of a measurement target cell (such as a blood cell) and has a great influence on a measurement result. If the surface of the resin substrate is machined by the microfabrication such as the micromachining, manufacturing cost increases and it is, therefore, disadvantageously difficult to manufacture the cell analysis cartridge at low cost.
Citation List
Patent Literature
    [Patent Literature 1] JPA 2004-257768

SUMMARY OF INVENTION

Technical Problem

Accordingly, the present invention has been made to solve the conventional problems at least in part. It is a main object of the present invention not only to downsize a cartridge but also to constitute an aperture simply and at low cost while making use of a downsized configuration of the cartridge.
Solution to Problem A cell analysis cartridge according to one aspect of the present invention is a cell analysis cartridge including: a measurement channel circulating a measurement target fluid containing cells; an aperture provided on the measurement channel; and a pair of electrodes, fluid contact units being arranged at positions of the electrodes across the aperture, respectively, the cell analysis cartridge performing a cell analysis based on an impedance change between the electrodes caused by passing of the cells through the aperture, wherein the measurement channel includes: a first-surface-side channel unit provided on a first surface of a cartridge main body; a second-surface-side channel unit provided on a second surface of the cartridge main body; and a connection channel unit connecting the first-surface-side channel unit to the second-surface-side channel unit, and wherein the aperture is formed in the connection channel unit, the fluid contact unit of one of the electrodes is arranged in the first-surface-side channel unit, and the fluid contact unit of the other electrode is arranged in the second-surface-side channel unit.

With a configuration according to one aspect of the present invention, by configuring the measurement channel to include the first-surface-side channel unit, the second-surface-side channel unit, and the connection channel unit, it is possible to form the measurement channel unit on first and second surfaces of the cartridge main body and to make a plane size of the cell analysis cartridge compact. In this case, the aperture is provided in the connection channel, whereby the fluid contact unit of one electrode can be arranged on the first surface of the cartridge main body and the fluid contact unit of the other electrode can be arranged on the second surface of the cartridge main body. Due to this, the aperture does not prevent the cartridge from being made compact. Furthermore, there is no need to machine a base material to form a fine groove for forming the aperture but the aperture can be constituted out of a through-hole formed in the connection channel unit. Therefore, the aperture can be constituted simply and at low cost.

To simplify the configuration of the aperture, decrease the number of components, and reduce manufacturing cost, it is preferable that the aperture is formed by narrowing a channel cross-sectional area of the connection channel unit.

It is also preferable that the aperture is formed by an aperture formation member provided in a first-surface-side opening or a second-surface-side opening of the connection channel unit. By so forming, the cartridge main body in which the first-surface-side channel unit, the second-surface-side channel unit, and the connection channel unit are formed and the aperture formation member can be made as separate components. Even if cartridges including apertures different in size are to be manufactured, it suffices to select only aperture formation members, while using the common cartridge main body. It is possible to decrease the number of components and reduce the manufacturing cost.

Furthermore, it is preferable to provide a body fluid analyzer that is the body fluid analysis cartridge and that includes the measurement channel and the mixture channel as follows so as to constitute the body fluid analyzer to be made compact while making the capacity of the mixture channel as large as possible.

A body fluid analyzer according to another aspect of the present invention is a body fluid analyzer including: a measurement channel circulating a measurement target fluid obtained by diluting a body fluid with a diluent, the measurement channel including a detecting unit detecting the measurement target fluid by physical means or chemical means; a mixture channel provided upstream of the measurement channel, and agitating the body fluid and the diluent; and an analyzer main body, the measurement channel and the mixture channel being formed in the analyzer main body, wherein the mixture channel includes: a first-surface-side channel unit provided on a first surface of the analyzer main body; a second-surface-side channel unit provided on a second surface of the analyzer main body; and a connection channel unit connecting the first-surface-side channel unit to the second-surface-side channel unit.

With a configuration according to another aspect of the present invention, by configuring the mixture channel to include the first-surface-side channel unit, the second-surface-side channel unit, and the connection channel unit, the mixture channel can be formed in a thickness direction and a plane size of the body fluid analyzer can be made compact while making the capacity of the mixture channel as large as possible. Since the capacity of the mixture channel can be made as large as possible, it is possible to uniformly mix up the body fluid and the diluent and to thereby improve body-fluid analytical precision.

It is preferable that the analyzer main body includes a thick portion and a thin portion, a reservoir holder accommodating a diluent reservoir storing the diluent and the mixture channel are formed in the thick portion, and that the measurement channel is formed in the thin portion. By doing so, it is possible to form the mixture channel while making effective use of a sidewall of the reservoir holder accommodating the diluent reservoir, and to make the capacity of the mixture channel as large as possible.

It is preferable that the thick portion and the thin portion are formed so that a rear surface of the thick portion is flush with a rear surface of the thin portion, the measurement channel is formed on the rear surface of the thin portion, and the measurement channel is connected to the second-surface-side channel unit provided on the rear surface of the thick portion. By doing so, it is possible to simplify machining of the first-surface-side channel unit, the second-surface-side channel unit, and the measurement channel for the analyzer main body.

It is preferable that the reservoir holder accommodates the diluent reservoir such that a central axis of the diluent reservoir is along a plane direction of the reservoir holder. In this case, if the diluent reservoir is a reservoir elongated in the central axis direction, it is possible to reduce a volume of a rectangular parallelepiped circumscribed about the body fluid analyzer and to constitute the body fluid analyzer to be made compact.

Advantageous Effects of Invention

According to the present invention constituted as stated above, it is possible not only to downsize the cartridge but also to constitute the aperture simply and at low cost while making use of the downsized configuration of the cartridge.

DETAILED DESCRIPTION OF THE EMBODIMENTS

[First Embodiment]

Figure 1:
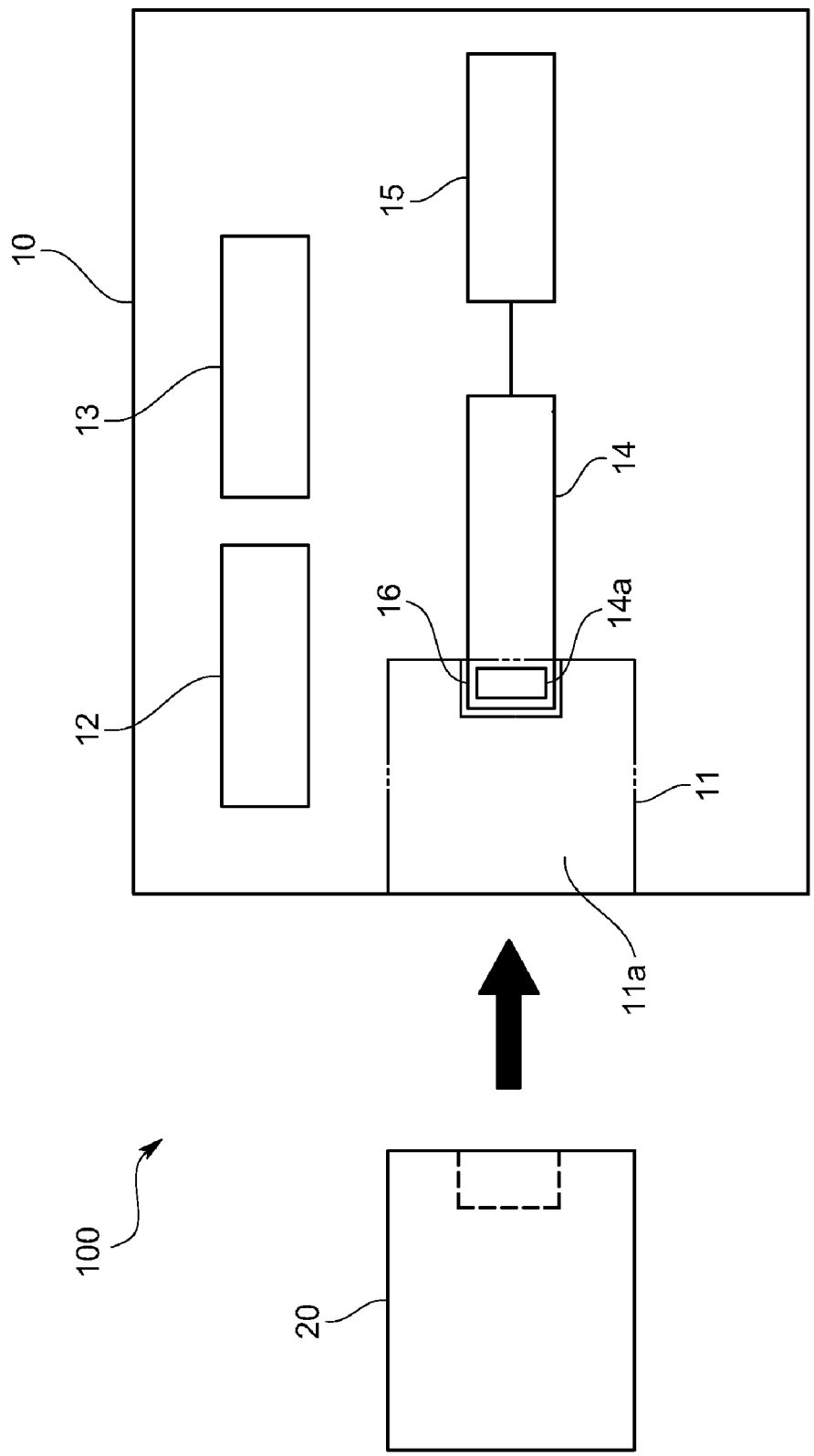
FIG. 1 is an overall perspective view schematically showing a configuration of a blood cell counter that is a body fluid analyzing apparatus according to an embodiment of the present invention.

A body fluid analyzing apparatus using a body fluid analyzer according to a first embodiment of the present invention is described referring to the drawings.

As shown in FIG. 1, a body fluid analyzing apparatus 100 according to the first embodiment includes a measurement-unit main body 10 and a cell analysis cartridge 20 (hereinafter, "cartridge 20") that is a body fluid analyzer detachably attached to the measurement-unit main body 10. The measurement-unit main body 10 includes an attachment unit 11 to which the cartridge 20 is attached, a driving unit 12 driving a sliding body 202 (to be described later) provided in the cartridge 20 to make a sliding movement and the like, a fluid supply unit 13 circulating a diluted sample blood (hereinafter, simply "diluted blood") that is a measurement target fluid in the cartridge 20, a connector 14 for fetching a signal from the cartridge 20, and an arithmetic unit 15 detecting an electric signal from the connector 14 and calculating the number and volume of blood cells contained in the diluted blood.

The attachment unit 11 includes a groove-like concave portion 11a (see FIG. 1) formed to be slightly larger than a width and a thickness of a tip end portion of the cartridge 20, which portion is a side edge portion for inserting the cartridge 20, and configured to have a predetermined depth according to a shape of the side edge portion for inserting the cartridge 20. A part (including a blood quantifying unit 22) of the cartridge 20 for grasping the cartridge 20 when the cartridge 20 is inserted into the concave portion 11a is located outside of the attachment unit 11. A protrusion 16 fitted into a notch 21 (see FIGS. 2, 3 and the like) formed in a tip end portion of the cartridge 20 is formed in an inner back portion of the concave portion 11a. A part (a conduction unit 14a) of the connector 14 contacting electrodes 27, 28, and 221 provided on the cartridge 20 and receiving an electric signal is formed on a front surface of the protrusion 16.

The driving unit 12 is configured to include an engagement claw engaged with an engagement unit 202a (an engagement hole, to be specific, see FIG. 3 and the like) provided in the sliding body 202 of the cartridge 20 and a slide driving mechanism (not shown) using, for example, a rack-and-pinion mechanism, a motor and the like for moving the engagement claw in a sliding direction. The driving unit 12 drives the sliding body 202 to slidably move between a blood quantifying position X (see FIG. 4) for quantifying the blood and a blood introduction position Y (see FIG. 5) for mixing the quantified blood with a reagent and introducing the mixture into a mixture channel 24 and a measurement channel 25. Note that the driving unit 12 also moves a through-needle 71 provided on the sliding body 202 toward a reagent reservoir 3 as described later.

The fluid supply unit 13 is configured to mainly include a suction pump and a switching valve. The suction pump is connected to an opening H on a terminal end of the measurement channel 25, to be described later, sets the terminal opening H to have a negative pressure, and attracts and introduces the quantified blood and the reagent into the mixture channel 24 and the measurement channel 25 when the cartridge 20 is attached to the attachment unit 11.

The connector 14 includes the conduction unit 14a electrically conducting to an inside of the concave portion 11a of the attachment unit 11. The conduction unit 14a contacts the electrodes 27 of the cartridge 20 when the cartridge 20 is attached to the attachment unit 11, applies a predetermined voltage between the electrodes 27, and detects a current amount proportional to a magnitude of electric resistance generated at a time of application of the predetermined voltage as an electric signal. The conduction unit 14a outputs this electric signal to the arithmetic unit 15 via an interconnection such as a lead wire.

The arithmetic unit 15 includes an electric circuit (not shown) that converts the electric signal output from the connector 14 into a pulse signal and that outputs the pulse signal as the number of blood cells contained in the diluted blood introduced into the measurement channel 25 and a volume of the blood cells. The output signal relating to the number and volume of blood cells is output to a display or the like.

A detailed configuration of the cartridge 20 is next described referring to FIGS. 2 to 9.

Figure 2:
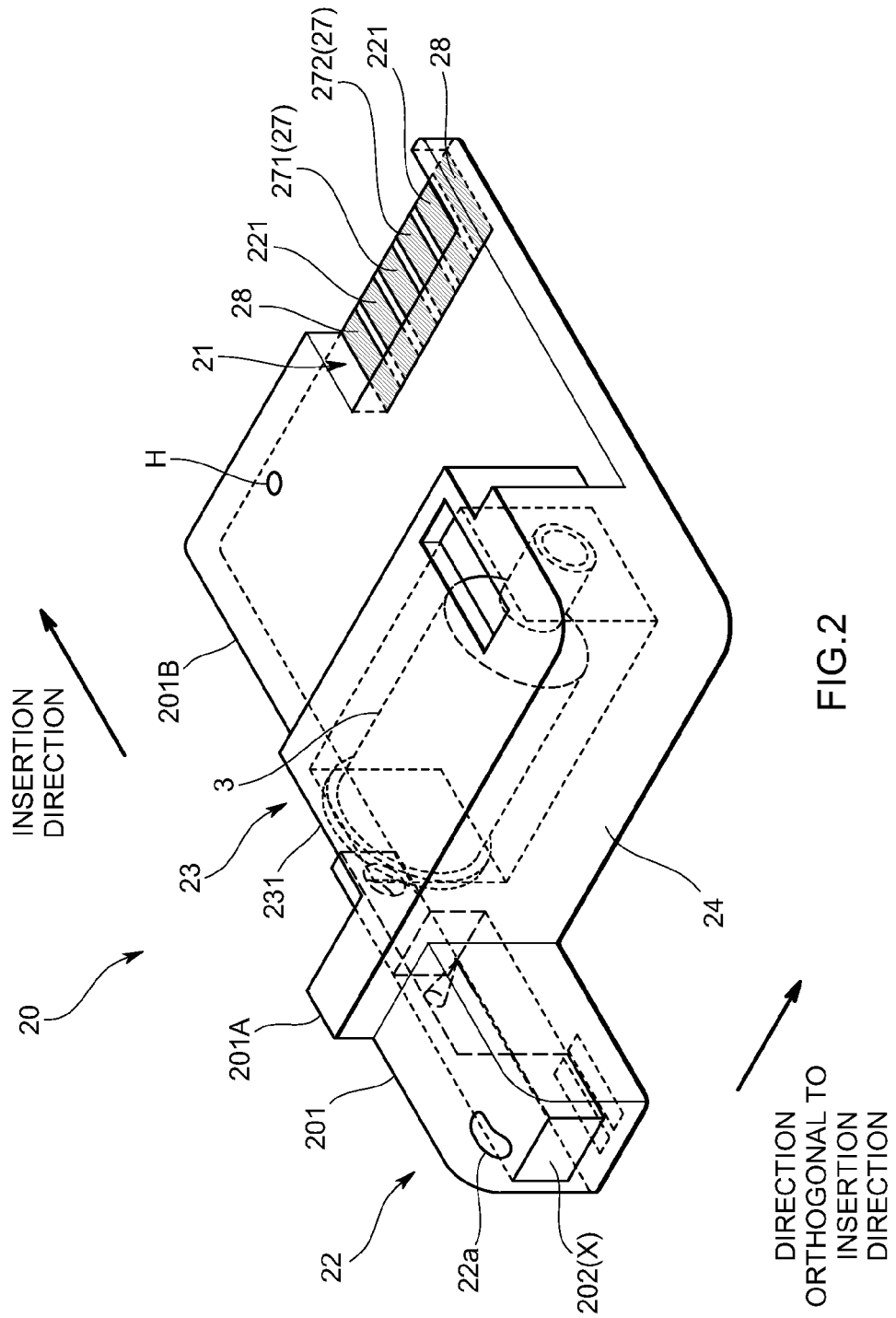
FIG. 2 is a perspective view of a cartridge according to the embodiment.
Figure 3:
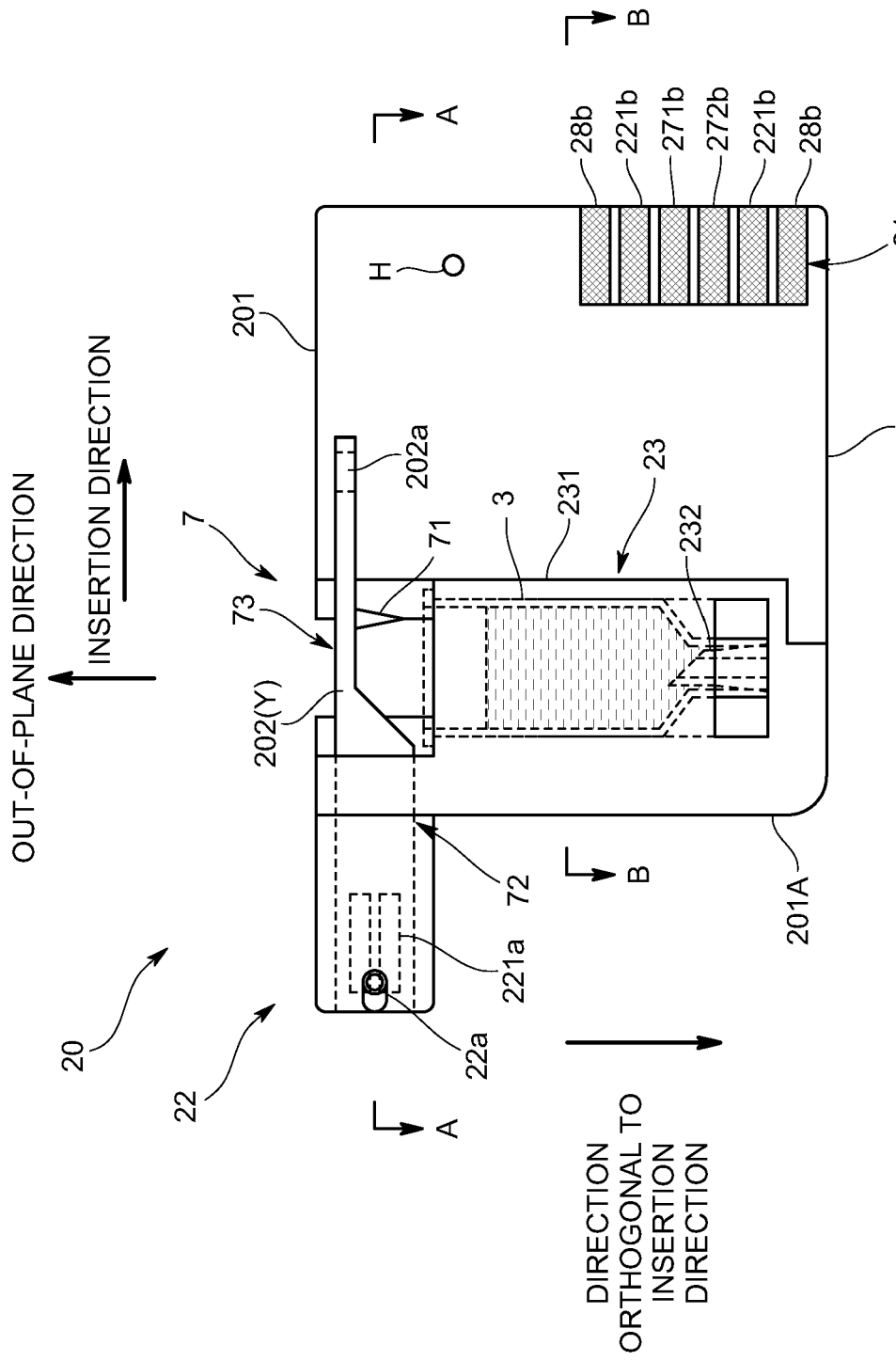
FIG. 3 is a plan view of the cartridge according to the embodiment.

As shown in FIGS. 2 and 3, the cartridge 20 is basically a single-use cartridge. The cartridge 20 includes the notch 21 having a generally rectangular cross-section and provided on a tip end of the cartridge 20 in an insertion direction, and the blood quantifying unit 22 that is provided near a generally central portion of an end of the cartridge 20 which end is distant from the tip end of the cartridge 20 in the insertion direction and that includes a blood introduction port 22a open in surfaces of the blood quantifying unit 22. This cartridge 20 also includes a reservoir holder 23 into which the reagent reservoir 3 for diluting the blood quantified by the blood quantifying unit 22 is attached, the mixture channel 24 for mixing up and agitating the quantified blood and the reagent from the reagent reservoir 3, and the measurement channel 25 for measuring the number of blood cells contained in the diluted blood generated by mixture of the blood and the reagent in the mixture channel 24.

Figure 4:
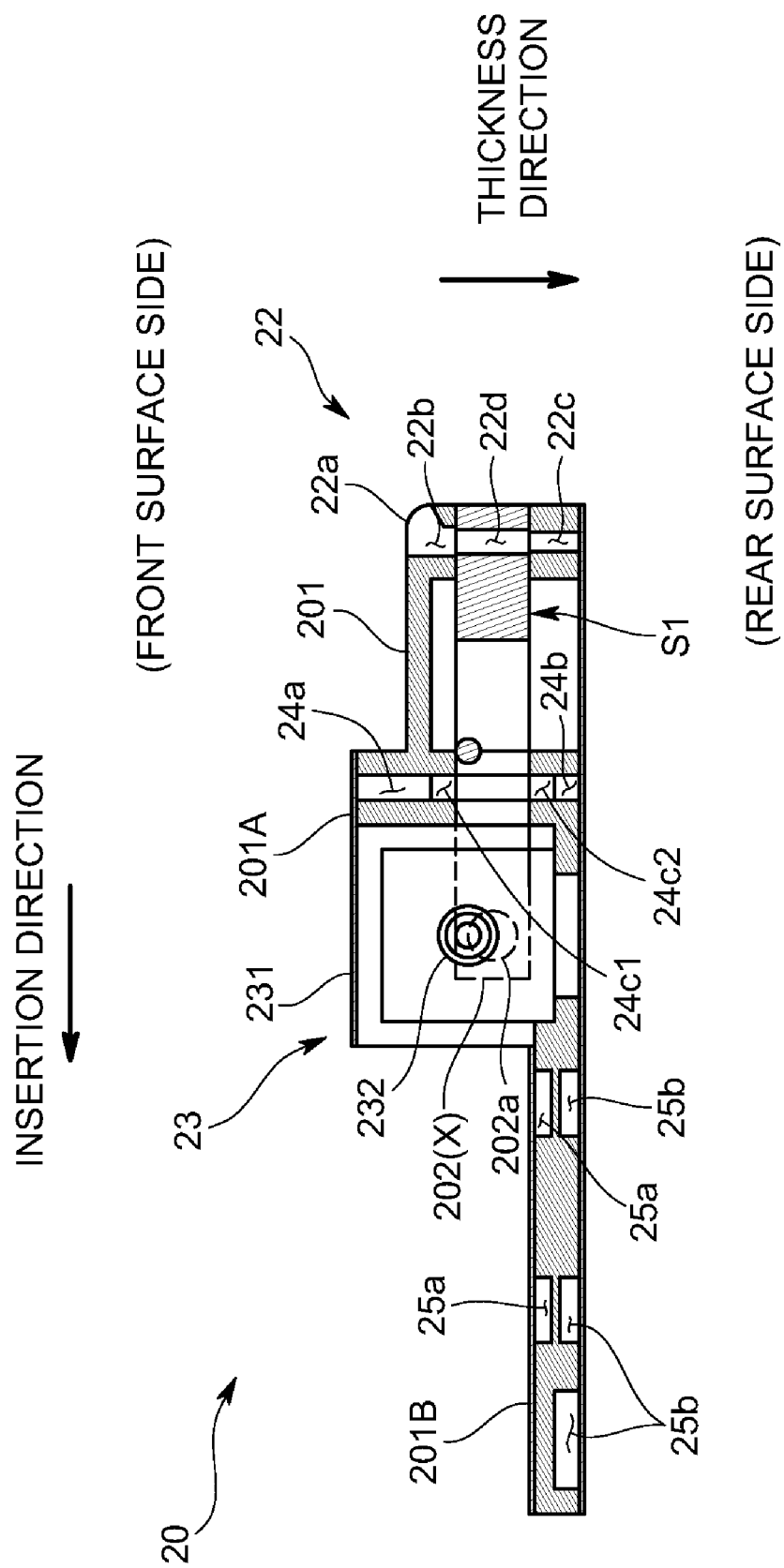
FIG. 4 is a cross-sectional view of the cartridge at a blood quantifying position, taken along a line A-A of FIG. 3 according to the embodiment.
Figure 5:
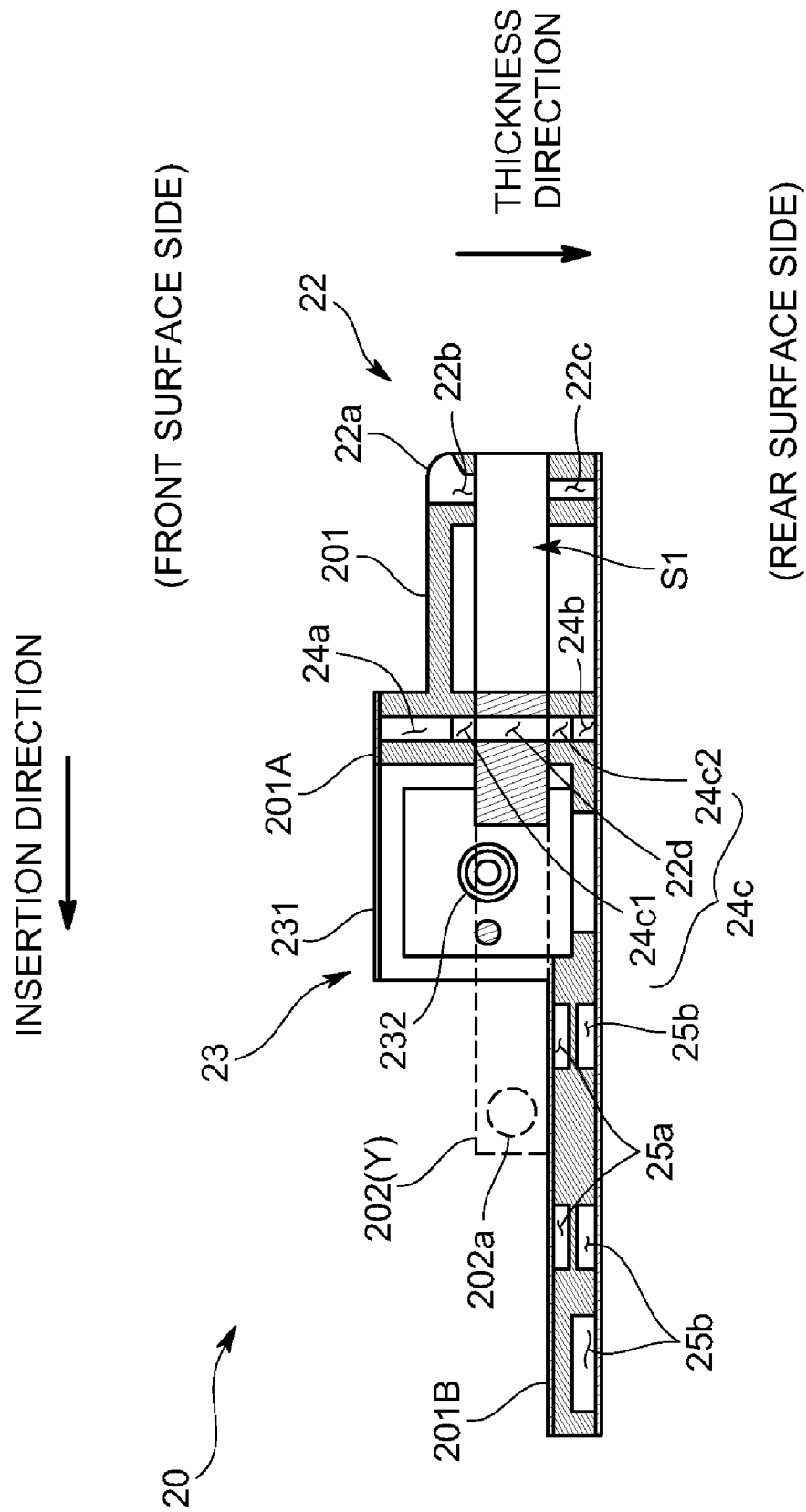
FIG. 5 is a cross-sectional view of the cartridge at a blood introduction position, taken along the line A-A of FIG. 3 according to the embodiment.

As shown in FIGS. 4 and 5, the blood quantifying unit 22 is configured to include a cartridge main body 201 that includes a generally linear upstream capillary channel 22b formed continuously to the upstream capillary channel 22b in the blood introduction port 22a and a generally linear downstream capillary channel 22c formed opposite to the upstream capillary channel 22b across a space 51 (space forming a sliding path for the sliding body 202 to be described later), and the sliding body 202 which is slidably provided in the space 51 and in which a quantifying capillary channel 22d communicating the upstream capillary channel 22b with the downstream capillary channel 22d and having a predetermined channel capacity for quantifying the blood introduced from the blood introduction port 22a is formed.

With this configuration, the engagement claw of the driving unit 12 is engaged with the engagement unit 202a formed on a tip end of the sliding body 202 in the insertion direction. The driving unit 12 drives the sliding body 202 to slidably move between the blood quantifying position X (FIG. 4) at which the quantifying capillary channel 22d communicates the upstream capillary channel 22b with the downstream capillary channel 22d, and the blood introduction position Y (FIG. 5) at which the quantifying capillary channel 22d communicates a front-surface-side connection channel unit 24c1 and a rear-surface-side connection channel unit 24c2, to be described later, with each other. Note that in a state in which the quantifying capillary channel 22d, the front-surface-side connection channel unit 24c1, and the rear-surface-side connection channel unit 24c2 communicate with one another, the quantifying capillary channel 22d, the front-surface-side connection channel unit 24c1, and the rear-surface-side connection channel unit 24c2 constitute a connection channel unit 24c connecting the front-surface-side channel unit 24a to the rear-surface-side channel unit 24b.

To detect that the quantifying capillary channel 22d is filled with blood, a fluid sensor 221 detecting whether the blood has arrived is provided downstream of the downstream capillary channel 22c as shown in FIGS. 2 and 3. This fluid sensor 221 is configured to include a fluid contact unit 221a constituted by electrodes and provided to close either entirely or partially a downstream opening of the downstream capillary channel 22c, a lead wire (not shown) led out from the fluid contact unit 221a, and a signal fetching unit 221b appearing on a front surface of the cartridge 20 below the notch 21 to electrically conduct to the fluid contact unit 221a via the lead wire.

The reservoir holder 23 is a holder to which the reagent reservoir 3 serving as an analysis fluid reservoir is detachably attached. Specifically, as shown in FIGS. 3 to 6, the reservoir holder 23 includes a reservoir accommodation unit 231 which is provided in a thick portion 201A of the cartridge main body 201 and into which the reagent reservoir 3 is inserted and accommodated from a transverse direction (orthogonal to the insertion direction), and a reagent-lead needle 232 provided to extend from a bottom wall of the reservoir accommodation unit 231 and penetrating through a seal 32 of the reagent reservoir 3 accommodated in the reservoir accommodation unit 231. An inner channel of the reagent-lead needle 232 communicates with the mixture channel 24 (a front-surface-side channel unit 24a) formed on a front surface of the reservoir holder 23 (that is, a front surface of the thick portion 201A of the cartridge main body 201).

Figure 8:
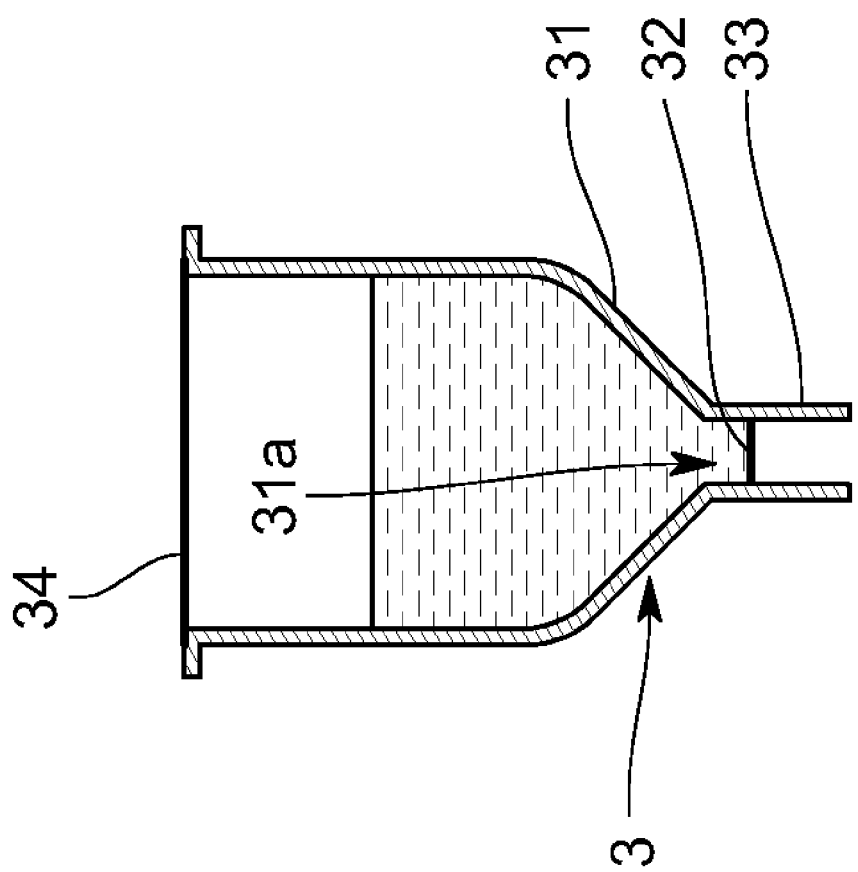
FIG. 8 is a cross-sectional view showing a configuration of a reagent reservoir according to the embodiment.

The reagent reservoir 3 accommodates the reagent that is an analysis fluid of a predetermined quantity. As shown in FIG. 8, the reagent reservoir 3 includes a reservoir main body 31 on a bottom wall of which an opening 31a that can let out the reagent to an outside of the reagent reservoir 3 is formed, the seal 32 sealing the opening 31a, and a guide 33 provided outside of the seal 32 and formed into a generally cylindrical shape.

The reservoir main body 31 is generally shaped as a body of revolution, a larger axial size than a radial size, and the bottom wall of a funnel shape. The opening 31a is formed almost in a central portion of the bottom wall. The guide 33 is provided to cover up a circumference of the seal 32, guides to insert the reagent-lead needle 232 to penetrate through the seal 32, and contacts an outer circumference of the reagent-lead needle 232 almost fluid-tightly when the reagent-lead needle 232 penetrates through the seal 32. The reagent reservoir 3 according to the first embodiment is made of resin such as polypropylene and the reservoir main body 31, the seal 32, and the guide 33 are formed integrally into the reagent reservoir 3. An upper portion of the reagent reservoir 3 is open as an upper opening. The upper opening of the reagent reservoir 3 is hermetically sealed with a sealing film 34 such as an aluminum film serving as a sealing member after accommodating therein the reagent from the upper opening. The reagent reservoir 3 configured as stated above is accommodated in the reservoir accommodation unit 231 such that an axial direction of the reagent reservoir 3 is orthogonal to the insertion direction in a plan view.

Figure 6:
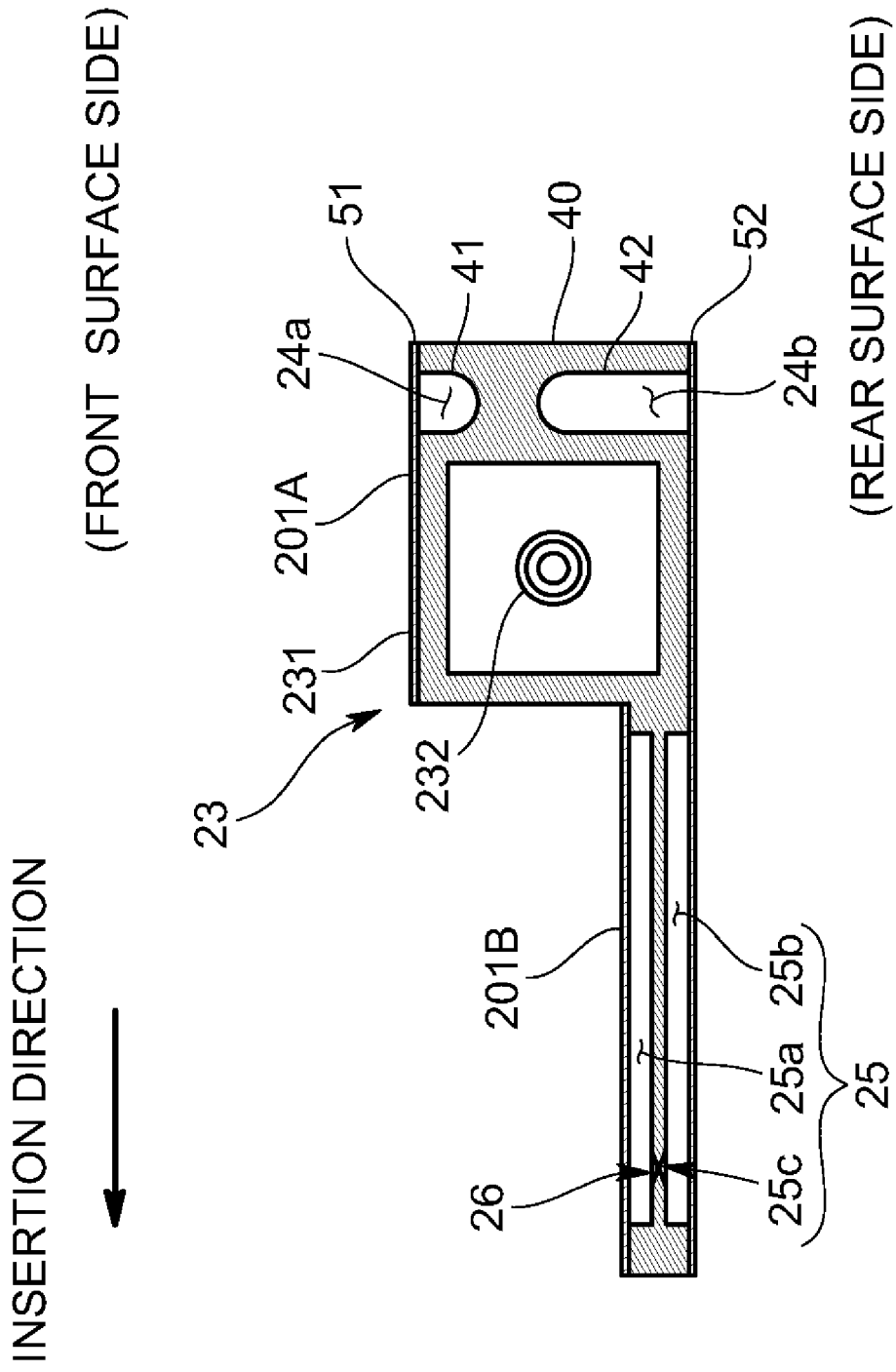
FIG. 6 is a cross-sectional view of the cartridge, taken along a line B-B of FIG. 3 according to the embodiment.

The mixture channel 24 is formed on a front surface that is a first surface of the thick portion 201A of the cartridge main body 201 and a rear surface that is a second surface thereof. The mixture channel 24 mixes up and agitates the blood quantified by the quantifying capillary channel 22d of the sliding body 202 and the reagent from the reagent reservoir 3. Specifically, as shown in FIGS. 4 to 6, the mixture channel 24 is configured to include the front-surface-side channel unit 24a that is a first-surface-side channel unit formed on a front surface of a sidewall of the reservoir accommodation unit 231 of the reservoir holder 23, a rear-surface-side channel unit 24b that is a second-surface-side channel unit formed on a rear surface of the sidewall of the reservoir accommodation unit 231, and a connection channel unit 24c formed in a sidewall thickness direction of the reservoir accommodation unit 231 and connecting the front-surface-side channel unit 24a to the rear-surface-side channel unit 24b.

The front-surface-side channel unit 24a is formed on the front surface of the sidewall of the reservoir accommodation unit 231 in the direction orthogonal to the insertion direction. Further, the front-surface-side channel unit 24a has an upstream opening communicating with the inner channel of the reagent-lead needle 232 and a downstream opening communicating with an upstream opening of the connection channel unit 24c.

Similarly to the front-surface-side channel unit 24a, the rear-surface-side channel unit 24b is formed on the rear surface of the sidewall of the reservoir accommodation unit 231 in the direction orthogonal to the insertion direction. Further, the rear-surface-side channel unit 24b has an upstream opening communicating with a downstream opening of the connection channel unit 24c and a downstream opening communicating with an upstream opening of the measurement channel 25. Moreover, the downstream opening of the front-surface-side channel unit 24a and the upstream opening of the rear-surface-side channel unit 24b configured as stated above are formed to substantially overlap in a plan view.

The connection channel unit 24c has the upstream opening communicating with the downstream opening of the front-surface-side channel unit 24a and the downstream opening communicating with the upstream opening of the rear-surface-side channel unit 24b. The connection channel unit 24c connects the front-surface-side channel unit 24a to the rear-surface-side channel unit 24b in a thickness direction.

Specifically, the connection channel unit 24c is configured to include the front-surface-side connection channel unit 24c1 communicating with the downstream opening of the front-surface-side channel unit 24a, the rear-surface-side connection channel unit 24c2 formed opposite to the front-surface-side connection channel unit 24c1 across the space 51 (space forming the sliding path for the sliding body 202) and communicating with the upstream opening of the rear-surface-side channel unit 24b, and the quantifying capillary channel 22d of the sliding body 202 slidably provided in the space 51. The front-surface-side connection channel unit 24c1 has one end communicating with the front-surface-side channel unit 24a and the other end opening to the space 51. The rear-surface-side connection channel unit 24c2 has one end opening to the space 51 and the other end communicating with the rear-surface-side channel unit 24b.

That is, if the sliding body 202 is at the blood quantifying position X, the connection channel unit 24c is not formed. Accordingly, the front-surface-side channel unit 24a does not communicate with the rear-surface-side channel unit 24b (see FIG. 4). If the sliding body 202 is at the blood introduction position Y, the connection channel unit 24c is formed. Accordingly, the front-surface-side channel unit 24a communicates with the rear-surface-side channel unit 24b (see FIG. 5). In this way, if the sliding body 202 is at the blood introduction position Y, then the connection channel unit 24c is formed, and the quantified blood is introduced into the mixture channel 24. In this state, attraction of the reagent by the fluid supply unit 13 enables the reagent to be introduced into the front-surface-side channel unit 24a, the connection channel unit 24c, and the rear-surface-side channel unit 24b from the inner channel of the reagent-lead needle 232 inserted into the reagent reservoir 3. Further, as a result of attraction and discharge operations performed by the suction pump of the fluid supply unit 13, the quantified blood and the reagent are mixed up and a diluted blood is produced in the mixture channel 24.

As shown in FIG. 6, the thick portion 201A of the cartridge main body 201 is configured to include a base material 40 made of, for example, PMMA and having bottomed grooves 41 and 42 for the front-surface-side channel unit 24a and the rear-surface-side channel unit 24b formed on front and rear surfaces of the thick portion 201A, respectively, and a front-surface film 51 and a rear-surface film 52 serving as PET cover members bonded onto front and rear surfaces of the base material 40 via adhesive sheets, respectively. The blood quantifying unit 22 and the reservoir holder 23 are formed in a thick portion of the base material 40.

In this way, by configuring the mixture channel 24 to include the front-surface-side channel unit 24a, the rear-surface-side channel unit 24b, and the connection channel unit 24c, the mixture channel 24 can be formed in a thickness direction of the cartridge main body 201 and a plane size of the cartridge 20 can be made compact while making a capacity of the mixture channel 24 as large as possible. In the first embodiment, in particular, the front-surface-side channel unit 24a and the rear-surface-side channel unit 24b are formed on a sidewall of the reservoir holder 23 that corresponds to the thick portion 201A of the cartridge main body 201 in the sidewall thickness direction. This can make the capacity of the mixture channel 24 as large as possible. Furthermore, since the capacity of the mixture channel 24 can be made as large as possible, it is possible to uniformly mix up the blood that is a body fluid and the reagent that is a diluent and to thereby improve body-fluid analytical precision.

As shown in FIGS. 4 to 7, the measurement channel 25 is formed on a rear surface of a plane thin portion 201B that is a measurement-channel formation portion provided continuously to an insertion-side side surface of the thick portion 201A of the cartridge main body 201. This plane thin portion 201B is formed so that the rear surface of the plane thin portion 201B is flush with that of the thick portion 201A of the cartridge main body 201.

Specifically, as shown in FIG. 6, the measurement channel 25 is configured to include a front-surface-side channel unit 25a serving as a first-surface-side channel unit formed on a front surface that is a first surface of the thin portion 201B, a rear-surface-side channel unit 25b serving as a second-surface-side channel unit formed on a rear surface that is a second surface of the thin portion 201B, and a connection channel unit 25c formed in a thickness direction of the thin portion 201B and connecting the front-surface-side channel unit 25a to the rear-surface-side channel unit 25b.

The front-surface-side channel unit 25a has an upstream opening communicating with the front-surface-side channel unit 24a of the mixture channel 24, and a downstream opening communicating with an upstream opening of the connection channel unit 25c.

The rear-surface-side channel unit 25b has an upstream opening communicating with a downstream opening of the connection channel unit 25c, and a downstream opening communicating with the opening H open on the surface of the cartridge main body 201.

The connection channel unit 25c is formed on a partition wall dividing the front-surface-side channel unit 25a from the rear-surface-side channel unit 25b in a thickness direction of the partition wall. The connection channel unit 25c has the upstream opening communicating with the downstream opening of the front-surface-side channel unit 25a and the downstream opening communicating with the upstream opening of the rear-surface-side channel unit 25b, and connects the front-surface-side channel unit 25a to the rear-surface-side channel unit 25b in the thickness direction.

Figure 7:
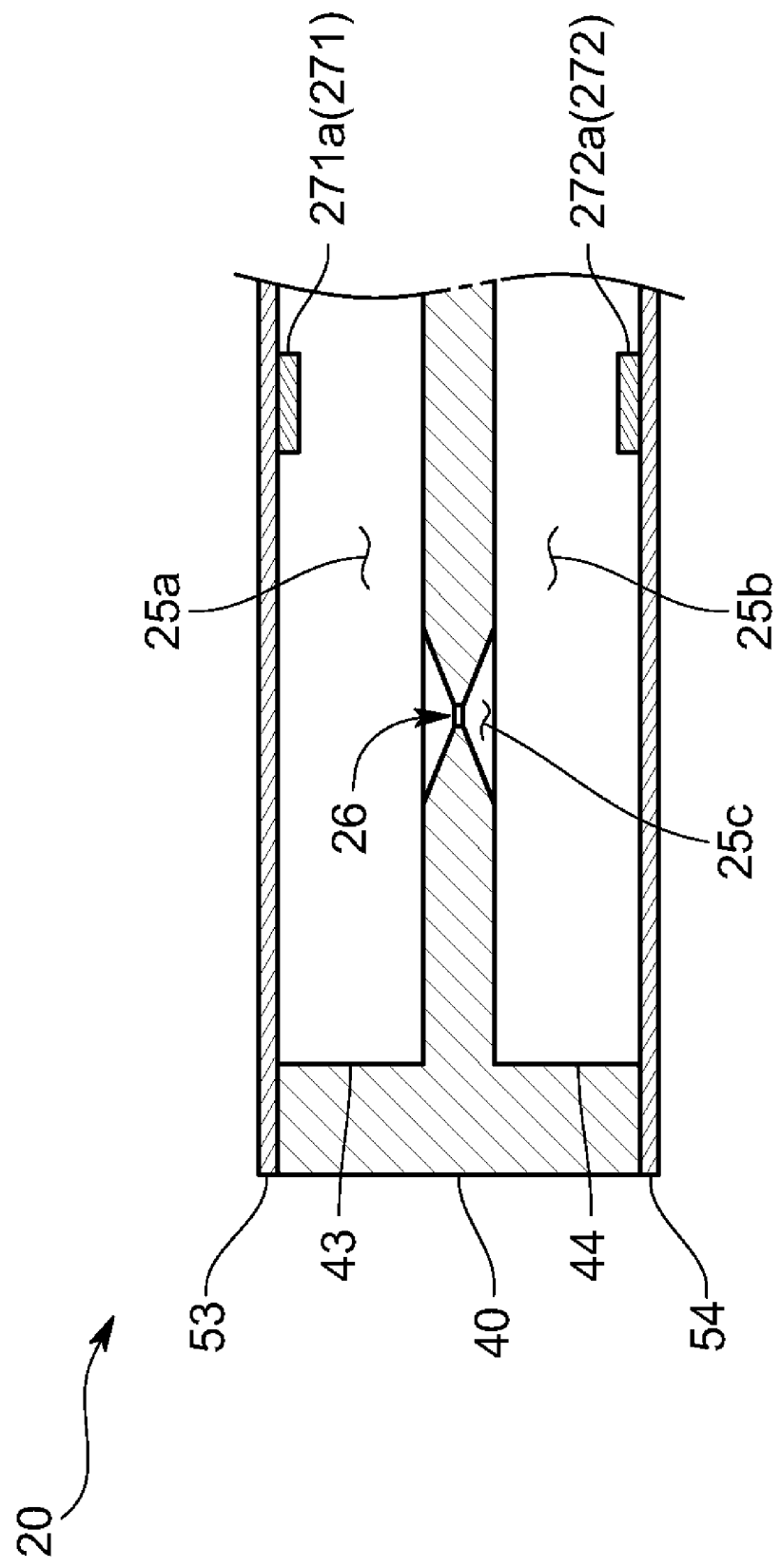
FIG. 7 is an enlarged cross-sectional view typically showing a measurement channel and an aperture according to the embodiment.

As shown in FIGS. 6 and 7, in the cartridge 20 according to the first embodiment, an aperture 26 is formed in the connection channel unit 25c, and a pair of electrodes 27 serving as detecting units are arranged across the aperture 26 on the front-surface-side channel unit 25a and the rear-surface-side channel unit 25b that are channel units on both sides of the aperture 26, respectively. In FIG. 7, the electrodes 27 are denoted as a front-surface-side electrode 271 arranged on the front-surface-side channel unit 25a and a rear-surface-side electrode 272 arranged on the rear-surface-side channel unit 25b. The front-surface-side electrode 271 is configured to include fluid contact units 271a formed to face an inner wall of the front-surface-side channel unit 25a of the measurement channel 25, lead wires (not shown) led out from the respective fluid contact units 271a, and a signal fetching unit 271b appearing on the front surface of the cartridge 20 above the notch 21 to electrically conduct to the fluid contact units 271a via the lead wires. The rear-surface-side electrode 272 is configured to include fluid contact units 272a formed to face an inner wall of the front-surface-side channel unit 25b of the measurement channel 25, lead wires (not shown) led out from the respective fluid contact units 272a, and a signal fetching unit 272b appearing on the front surface of the cartridge 20 above the notch 21 to electrically conduct to the fluid contact unit 272a via the lead wire. Note that the signal fetching units 271b and 272b of the front-surface-side electrode 271 and the rear-surface-side electrode 272 are configured to electrically contact the conduction unit 14a of the connector 14 when the cartridge 20 is attached to the measurement-unit main body 10.

As shown in FIG. 7, the thin portion 201B of the cartridge main body 201 is configured to include the base material 40 made of, for example, PMMA and having bottomed grooves 43 and 44 for the front-surface-side channel unit 25a and the rear-surface-side channel unit 25b formed on front and rear surfaces of the thin portion 201B, respectively, and a front-surface film 53 and a rear-surface film 54 serving as PET cover members bonded onto the front and rear surfaces of the base material 40 via adhesive sheets, respectively. The electrodes 27 and 28 are formed on the front-surface-side film 53 and the rear-surface-side film 54, respectively to facilitate an inner configuration and assembly of the cartridge 20. By bonding the front-surface-side film 53 and the rear-surface-side film 54 onto the base material 40, the front-surface-side channel unit 25a and the rear-surface-side channel unit 25b are formed and the electrodes 27 and 28 are arranged in the channel units 25a and 25b, respectively. In the first embodiment, the rear surface of the thick portion 201A of the base material 40, that is, the rear surface of the base material 40 that constitutes the thick portion 201A is flush with the rear surface of the thin portion 201B, that is, the rear surface of the base material 40 that constitutes the thin portion 201B, so that the rear-surface-side film 52 and the rear-surface-side film 54 are considered one film.

The aperture 26 provided in the connection channel unit 25c is formed by narrowing a channel cross-sectional area of the connection channel unit 25c (see FIG. 7). That is, a channel of the connection channel unit 25c has a narrower diameter as being closer to a central portion from a front-surface-side opening of the connection channel unit 25c, and has a wider diameter as being closer to a rear-surface-side opening thereof from the central portion. With this configuration, the central portion of the connection channel unit 25c is formed as a minimum opening, thereby forming the aperture 26. For example, the minimum opening of the aperture 26 is a rectangular opening of 45 μm×40 μm. Since the aperture 26 can be formed as a part of the connection channel unit 25c, it is possible to simplify a configuration of the aperture 26, decrease the number of components, and reduce manufacturing cost. Note that the size of the minimum opening for forming the aperture 26 can be appropriately set according to a size of the measurement target cell (blood cell in the first embodiment).

Moreover, a second electrode 28 is provided downstream of the fluid contact unit 272a of the rear-surface-side electrode 272. The second electrode 28 is configured to include a fluid detecting unit (not shown) provided downstream of the fluid contact unit 272a (to be specific, upstream of the terminal end of the measurement channel 25 by a predetermined distance) and detecting whether a channel capacity of the measurement channel 25 is equal to a preset constant capacity, a lead wire (not shown) led out from the fluid detecting unit, and a detected-signal output unit 28b continuous to a terminal end of the lead wire and provided laterally of the signal fetching unit 272b. The second electrode 28 functions as a fluid level sensor that detects that the diluted blood has arrived at the fluid detecting unit.

That is, if the diluted blood flowing in the measurement channel 25 after contacting the fluid contact unit 272a contacts the fluid detecting unit of the second electrode 28, then an electric signal is generated, the electric signal is transmitted to the detected-signal output unit 28b via the lead wire led out from the liquid detecting unit, and arrival of the diluted blood at a predetermined arrival position in the measurement channel 25 is transmitted to the measurement-unit main body 10. If the arrival of the diluted blood at the predetermined position in the measurement channel 25 is detected, the fluid supply unit 13 stops supplying the diluted blood, thereby making it possible to prevent the diluted blood from arriving at the opening H on the terminal end of the measurement channel 25 and overflowing.

As shown in FIG. 3, the cartridge 20 according to the first embodiment includes an air opening mechanism 7 penetrating through the sealing film 34 of the reagent reservoir 3 accommodated in the reservoir holder 23 and opening the reagent reservoir 3 to the air.

This air opening mechanism 7 includes the through-needle 71 serving as a through-member penetrating through the sealing film 34 of the reagent reservoir 3 held in the reservoir holder 23, a first moving mechanism 72 moving the through-needle 71 in a direction orthogonal to a plane direction of the sealing film 34, and a second moving mechanism 73 moving the through-needle 71 in the plane direction of the sealing film 34.

Figure 9:
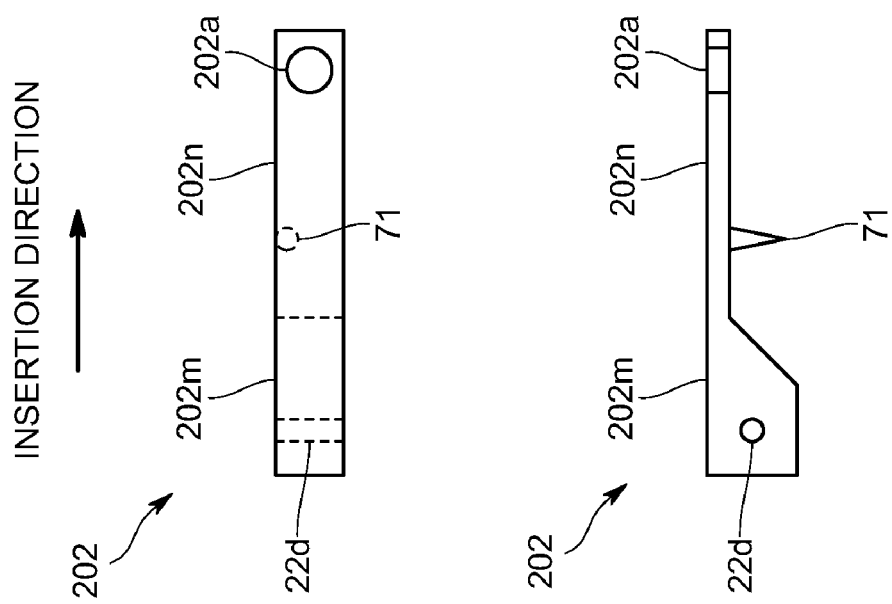
FIG. 9 illustrates a sliding body according to the embodiment.

The through-needle 71 is provided to face toward the reagent reservoir 3 on the tip end of the sliding body 202 serving as a holder holding the through-needle 71 in the insertion direction. As shown in FIG. 9, the sliding body 202 is configured to include a guided unit 202m forming the space S1 (sliding path) and sliding while contacting an inside surface of a sidewall of the cartridge main body 201, and an extension unit 202n provided to extend from the guided unit 202m in the insertion direction and thinner than the guided unit 202m. The through-needle 71 is provided on a reagent-reservoir 3-side of the extension unit 202n, and the engagement unit 202a described above is formed on the tip end side of the sliding body 202 relative to the through-needle 71.

Figure 10:
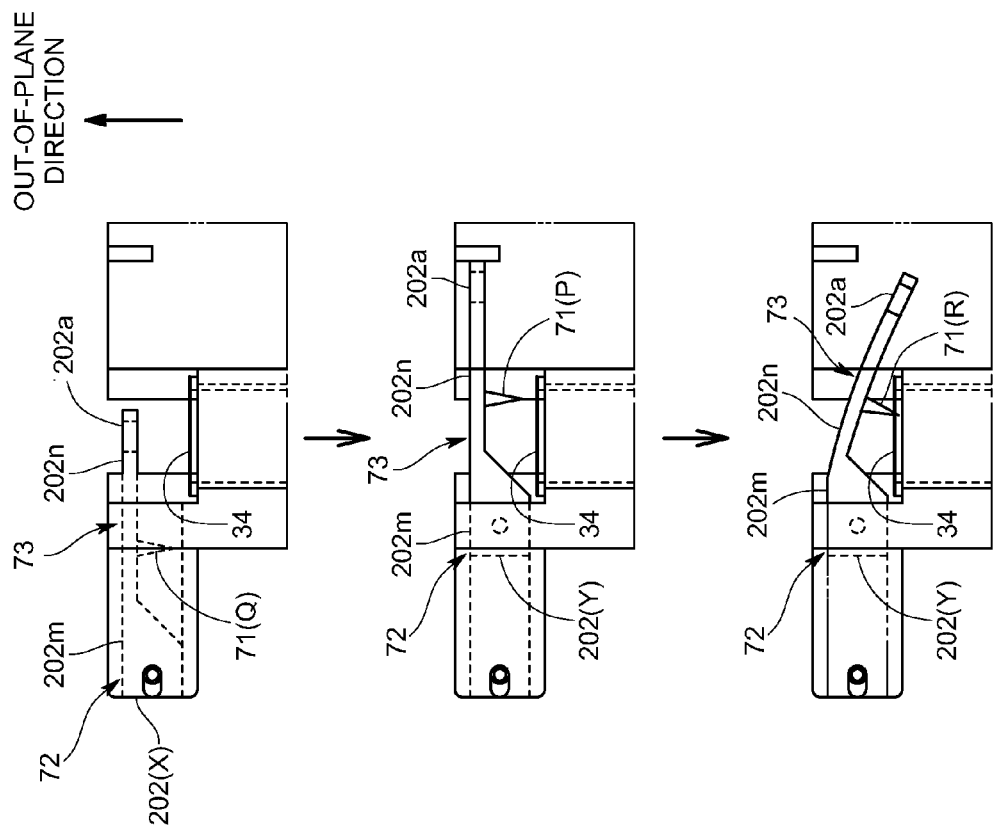
FIG. 10 illustrates operation performed by an air opening mechanism of the cartridge according to the embodiment.

As shown in FIG. 10, the first moving mechanism 72 allows the through-needle 71 to move between a hole-making position P upward of an out-of-plane direction of the sealing film 34 and a withdrawal position Q away from the hole-making position P in a direction orthogonal to the out-of-plane direction of the sealing film 34 (that is, in the insertion direction, the plane direction of the sealing film 34). Note that the withdrawal position Q is the position at which the through-needle 71 is not present upward of the out-of-plane direction of the sealing film 34 and which corresponds to the blood qualifying position X in the first embodiment.

Specifically, the first moving mechanism 72 is configured to include the guided unit 202m of the sliding body 202 and the sliding path serving as a guide provided in the cartridge main body 201. The first moving mechanism 72 allows the sliding body 202 to move forward and backward relative to the reagent reservoir 3 along the insertion direction. That is, the out-of-plane direction of the sealing film 34 of the reagent reservoir 3 is the direction in which an outside surface of the sealing film 34 faces and which is orthogonal to the plane direction of the sealing film 34.

The sliding body 202 moved by the first moving mechanism 72 configured as stated above is driven by the driving unit 12. That is, the engagement claw of the driving unit 12 is engaged with the engagement unit 202a of the sliding body 202, thereby moving the sliding body 202 from the withdrawal position Q to the hole-making position P (see FIG. 10).

That is, the quantifying capillary channel 22d and the through-needle 71 are provided in the sliding body 202. Note that a position of the sliding body 202 at which the quantifying capillary channel 22d is at the blood quantifying position X (position at which the upstream capillary channel 22b, the quantifying capillary channel 22d, and the downstream capillary channel 22c communicate with one another) is identical to a position of the sliding body 202 at which the through-needle 71 is at the withdrawal position Q. Furthermore, a position of the sliding body 202 at which the quantifying capillary channel 22d is at the blood introduction position Y (position at which the quantifying capillary channel 22d communicates with the measurement channel 25) is identical to a position of the sliding body 202 at which the through-needle 71 is at the hole-making position P.

As shown in FIG. 10, the second moving mechanism 73 allows the through-needle 71 moved to the hole-making position P by the first moving mechanism 72 to move toward the sealing film 34 and to move to a through position R at which the through-needle 71 penetrates through the sealing film 34. Note that the through position R is a position at which the through-needle 71 penetrates through the sealing film 34 to open the reagent reservoir 3 to the air.

Specifically, the second moving mechanism 73 is configured to include a bending unit provided between the guided unit 202m and a holding portion holding the through-needle 71 in the sliding body 202. The bending unit according to the first embodiment utilizes flexion resulting from an elastic deformation of the extension unit 202n.

The sliding body 202 moved by the second moving mechanism 73 configured as stated above is driven by the driving unit 12. That is, the engagement claw of the driving unit 12 is engaged with the engagement unit 202a of the sliding body 202, the engagement claw is moved toward the reagent reservoir 3, and the extension unit 202n of the sliding body 202 is pressed toward the reagent reservoir 3, thereby moving the through-needle 71 from the hole-making position P to the penetration position R (see FIG. 10).

The air opening mechanism 7 configured as stated above enables the through-needle 71 to perform a penetrating operation for penetrating through the sealing film 34 by being moved from the withdrawal position Q to the hole-making position P along the direction orthogonal to the plane direction of the sealing film 34 and then being moved to the penetration position R. Since the through-needle 71 is at the withdrawal position Q before the penetrating operation, it is possible to prevent the through-needle 71 from inadvertently contacting the sealing film 34 before the penetrating operation starts. Therefore, it is possible to prevent the reagent from leaking by preventing the sealing film 34 from being inadvertently broken by the through-needle 71.

Moreover, the sliding body 202 includes a cover located upward of the out-of-plane direction of the sealing film 34 and protecting the sealing film 34 from outside when the through-needle 71 is at the withdrawal position Q. In the first embodiment, the tip end side of the extension unit 202n relative to the through-needle 71 (portion at which the engagement unit 202a is provided) functions as the cover. This can prevent the sealing film 34 from being broken by contacting an external object other than the through-needle 71 in a state in which the through-needle 71 is at the withdrawal position Q.

[Measuring Procedures]

Procedures for measuring the number of blood cells and the size of each blood cell contained in the diluted blood using the body fluid analyzing apparatus 100 stated above are described next.

First, the reagent reservoir 3 is put into the reservoir holder 23 of the cartridge main body 201. At this moment, the reagent-lead needle 232 of the reservoir holder 23 does not penetrate through the seal 32 yet. The position of the sliding body 202 relative to the cartridge main body 201 is the blood quantifying position X. In this state, the cartridge 20 is attached to the measurement-unit main body 10. Thereafter, the reagent reservoir 3 is attached into the reservoir holder 23 and the reagent-lead needle 232 penetrates through the seal 32. At this time, the signal fetching unit 27b, the detected-signal output unit 28b, and the signal fetching unit 221b formed on the front surface of the cartridge main body 201 contact the conduction unit 14a of the connector 14. This conduction unit 14a supplies a small amount of current to the fluid sensor 221, the first electrode 27, and the second electrode 28 of the cartridge main body 201 so as to apply a predetermined voltage thereto.

Thereafter, the blood is attached to the blood introduction port 22a of the cartridge main body 201 present outside of the measurement-unit main body 10. Accordingly, capillary phenomena of the upstream capillary channel 22b, the quantifying capillary channel 22d, and the downstream capillary channel 22c introduce the attached blood into the upstream capillary channel 22b, the quantifying capillary channel 22d, and the downstream capillary channel 22c. At this time, the measurement-unit main body 10 acquires the detected signal from the fluid sensor 221 provided in the downstream opening of the downstream capillary channel 22c, and determines whether the blood has arrived at the downstream capillary channel 22c. If determining that the blood has arrived at the downstream capillary channel 22c, the measurement-unit main body 10 slides the sliding body 202 from the blood quantifying position X to the blood introduction position Y. At this time, the blood present outside of the quantifying capillary channel 22d is rubbed off by a formation wall forming the upstream capillary channel 22b and that forming the downstream capillary channel 22c, and only the blood held in the quantifying capillary channel 22d moves to the blood introduction position Y.

At this time, by pressing the extension unit 202n of the sliding body 202 toward the reagent reservoir 3, the measurement-unit main body 10 causes the through-needle 71 to penetrate through the sealing film 34 of the reagent reservoir 3 to open the reagent reservoir 3 to the air.

After the sliding body 202 moves to the blood introduction position Y, the fluid supply unit 13 operates to make an interior of the mixture channel 24 to have a negative pressure, and attracts the reagent from the reagent reservoir 3 into the mixture channel 24. Thereafter, the fluid supply unit 13 causes the suction pump to perform the attraction and discharge operations, thereby mixing up the blood and the reagent in the mixture channel 24 and/or reagent reservoir 3. After mixing, the fluid supply unit 13 attracts the diluted blood into the measurement channel 25.

If the diluted blood supplied into the measurement channel 25 passes through the aperture 26 and arrives at the paired fluid contact units 271a, the connector 14 detects electric resistance between the fluid contact units 271a via the signal fetching unit 271b as an electric signal. The electric signal is the pulse signal proportional to the electric resistance varying based on the number and volume (diameter) of the blood cells contained in the diluted blood passing through the aperture 26. The connector 14 calculates the number and volume of the blood cells contained in the diluted blood having passed through the aperture 26 for a predetermined time from the electric signal, and outputs a calculation result to the display or the like. Note that the predetermined time is a period, for example, from arrival of the diluted blood at the fluid contact unit 272a of the downstream electrode 272 to arrival thereof at the fluid detecting unit of the second electrode 28.

Moreover, if the diluted blood supplied into the measurement channel 25 passes through the position at which the fluid contact unit 272a of the downstream electrode 272 is provided and subsequently arrives at the position at which the fluid detecting unit of the second electrode 28 is provided, electric resistance of the second electrode 28 is detected via the detected-signal output unit 28b as an electric signal. If the connector 14 detects this electric signal, then the arithmetic unit 15 stops calculation, the switching valve of the fluid supply unit 13 is actuated, and the fluid supply unit 13 switches the opening H to communicate with the air. By doing so, the pressure of the opening H returns to atmospheric pressure and attraction of the diluted blood stops.

In this way, after measuring the number of blood cells contained in the diluted blood, the cartridge 20 is detached from the attachment unit 11, and the cartridge 20 in a state of accommodating the diluted blood therein is disposed of by a predetermined process such as incineration.

[Advantageous Effects of First Embodiment]

According to the body fluid analyzing apparatus 100 in the first embodiment configured as stated above, the measurement channel 25 is configured to include the front-surface-side channel unit 25a, the rear-surface-side channel unit 25b, and the connection channel unit 25c. It is thereby possible to form the measurement channel 25 on front and rear surfaces of the cartridge main body 201 and to make the plane size of the cartridge 20 compact. In this case, the aperture 26 is provided in the connection channel unit 25c, whereby the fluid contact unit 271a of one electrode 271 can be arranged on the front surface of the cartridge main body 201 and the fluid contact unit 272a of the other electrode 272 can be arranged on the rear surface of the cartridge main body 201. Due to this, the aperture 26 does not prevent the cartridge 20 from being made compact. Furthermore, there is no need to machine the base material 40 to form a fine groove for forming the aperture 26 but the aperture 26 can be constituted of the opening formed in the connection channel unit 25c. Therefore, the aperture 26 can be constituted simply and at low cost.

The present invention is not limited to the first embodiment.

Figure 11:
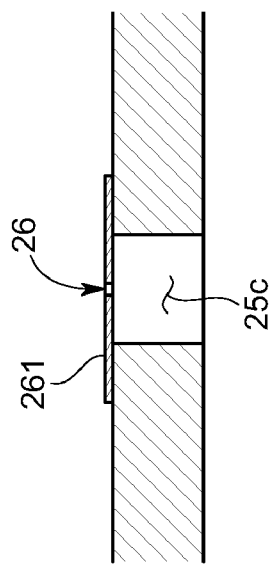
FIGS. 11A, 11B, and 11C illustrate modifications of the aperture of the cartridge according to the embodiment.
Figure 11:
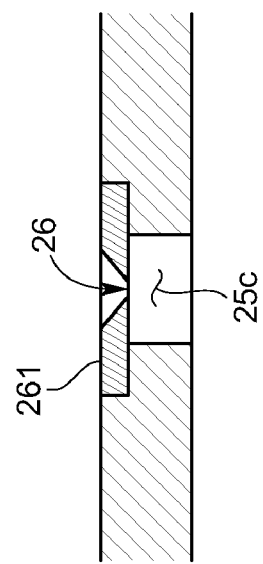
Figure 11:
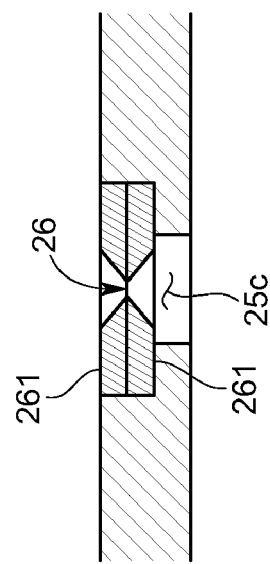

For example, as a method of forming the aperture 26, aside from the first embodiment, the aperture 26 can be constituted by arranging an aperture formation member 261 having a through-hole of a predetermined size (for example, rectangular hole of 45 μm×40 μm) upstream or downstream of the connection channel unit 25c, as shown in FIGS. 11A, 11B, and 11C. If the aperture 26 is formed out of the aperture formation member 261, the through-hole can be formed in, for example, a PET sheet (see FIG. 11A), or the generally rectangular through-hole can be formed by, for example, anisotropically etching a silicon substrate (see FIG. 11B). To set the through-hole formed in the silicon substrate to have a size of about 45 μm×45 μm, a thickness of the silicon substrate is set to about 50 μm. Alternatively, to prevent sediment of the diluted blood downstream of the aperture 26 constituted by forming the through-hole in the silicon substrate, the aperture 26 can be formed by bonding rear surfaces of etched silicon substrates (see FIG. 11C).

While the aperture 26 is formed by narrowing the channel cross-sectional area of the connection channel unit 25c according to the first embodiment, the aperture 26 can be formed as a part of the connection channel unit 25c without narrowing the channel cross-sectional area of the connection channel unit 25c.

Furthermore, the body fluid analyzing apparatus 100 according to the first embodiment is configured so that the connection channel unit 24c of the mixture channel 24 includes the front-surface-side connection channel unit 24c1, the quantifying capillary channel 22d, and the rear-surface-side connection channel unit 24c2, and that the connection channel unit 24c is used to introduce the quantified blood into the mixture channel 24. However, the present invention is not limited to the first embodiment. That is, the body fluid analyzing apparatus 100 can be configured so as not to use the connection channel unit 24c to introduce the quantified blood into the mixture channel 24 but to use the connection channel unit 24c only for connecting the front-surface-side channel unit 24a to the rear-surface-side channel unit 24b.

Moreover, while the mixture channel 24 is formed only on the front and rear surfaces of the reservoir holder 23 in the first embodiment, the mixture channel 24 can be formed to spread through the thin portion 201B of the cartridge main body 201.

Furthermore, the measurement channel 25 according to the first embodiment can be formed in the thick portion 201A of the cartridge main body 201, that is, on the front and rear surfaces of the reservoir holder 23.

Additionally, according to the first embodiment, the first-surface-side channel units and the second-surface-side channel units of the measurement channel 25 and the mixture channel 24 are the front-surface-side channel units 25a and 24a and the rear-surface-side channel units 25b and 24b, respectively. Alternatively, the other side surfaces can be assumed as first or second surfaces and the first-surface-side channel units or second-surface-side channel units can be formed on the other side surfaces.

Moreover, the body fluid analyzing apparatus 100 is employed to calculate the number of blood cells according to the first embodiment. Alternatively, the body fluid analyzing apparatus 100 can be employed for other analysis purposes (such as an analysis of a particle size distribution) for particles of cells or the like contained in a measurement target fluid.

[Second Embodiment]

A mixture channel and a measurement channel according to a second embodiment are described.

The mixture channel 24 is formed on the front surface that is the first surface of the thick portion 201A of the cartridge main body 201 and the rear surface that is the second surface thereof. The mixture channel 24 mixes up and agitates the blood quantified by the quantifying capillary channel 22d of the sliding body 202 and the reagent from the reagent reservoir 3. Specifically, as shown in FIGS. 12 to 16, the mixture channel 24 is configured to include the front-surface-side channel unit 24a that is the first-surface-side channel unit formed on the front surface of the sidewall of the reservoir accommodation unit 231 of the reservoir holder 23, the rear-surface-side channel unit 24b that is the second-surface-side channel unit formed on the rear surface of the sidewall of the reservoir accommodation unit 231, and the connection channel unit 24c formed in the sidewall thickness direction of the reservoir accommodation unit 231 and connecting the front-surface-side channel unit 24a to the rear-surface-side channel unit 24b.

Figure 12:
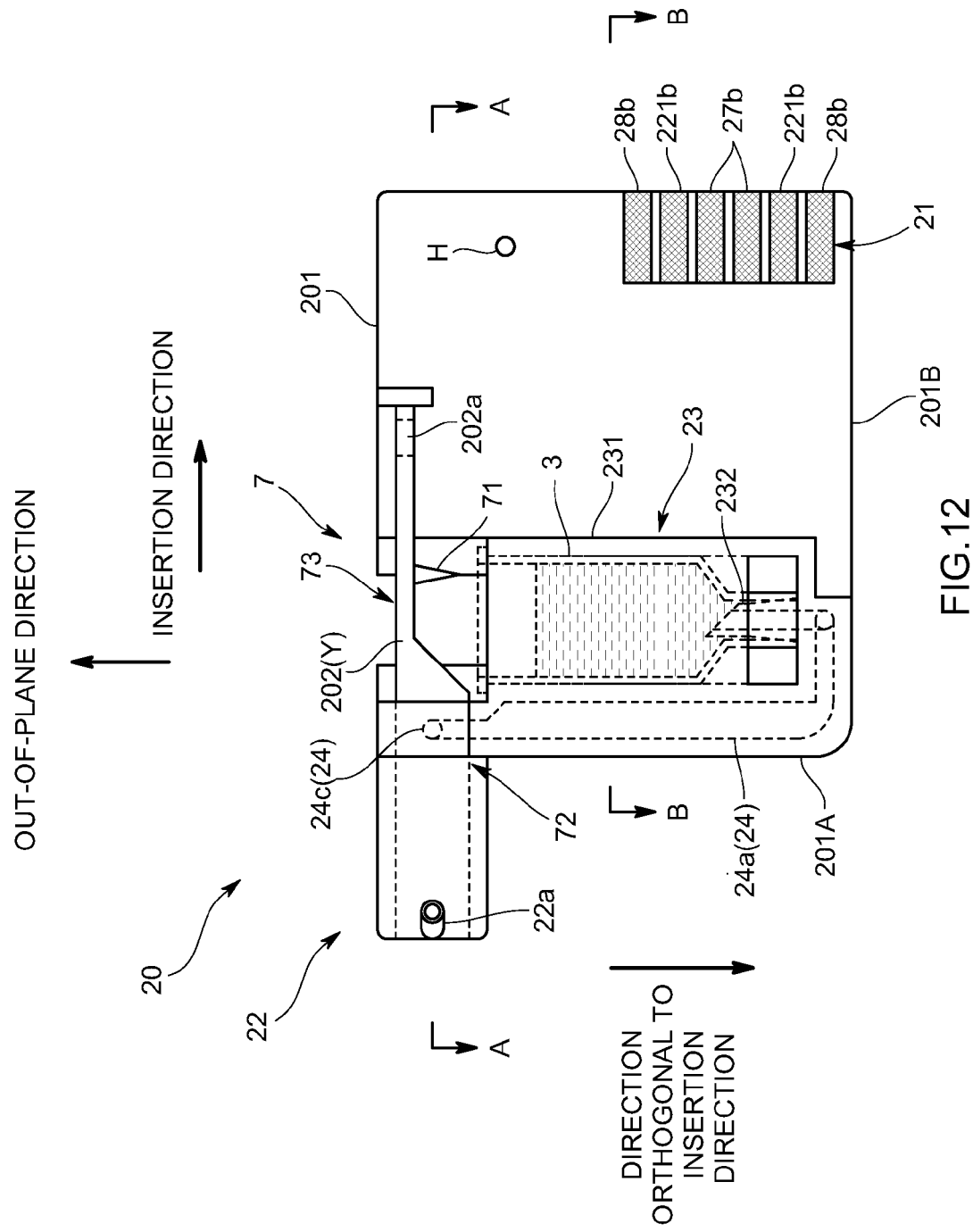
FIG. 12 is a front view showing a channel and the like formed on a front surface of the cartridge according to another embodiment.

As particularly shown in FIG. 12, the front-surface-side channel unit 24a is formed on the front surface of the sidewall of the reservoir accommodation unit 231 in the direction orthogonal to the insertion direction in a plan view. Further, the front-surface-side channel unit 24a has the upstream opening communicating with the inner channel of the reagent-lead needle 232 and the downstream opening communicating with the upstream opening of the connection channel unit 24c.

Figure 13:
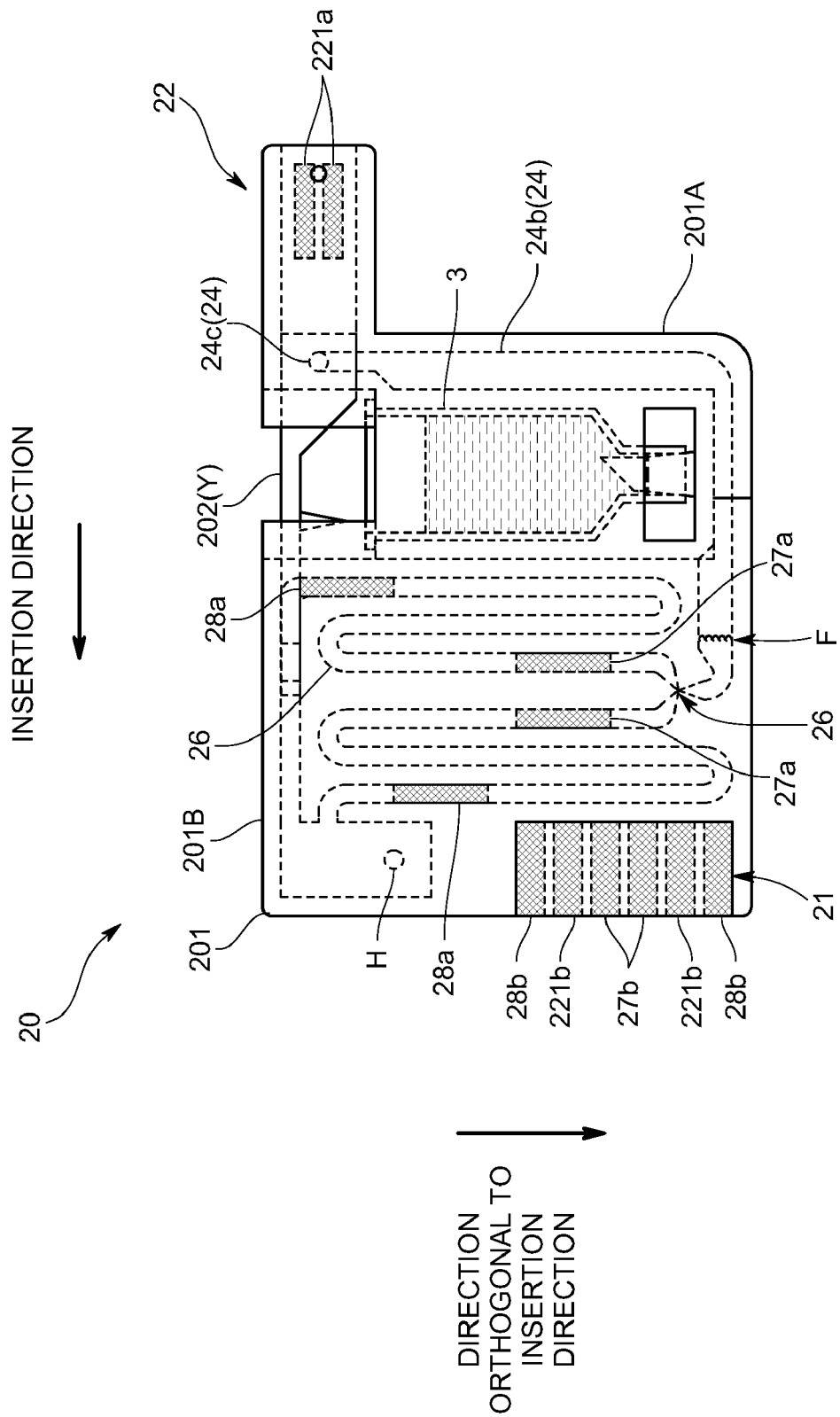
FIG. 13 is a rear view showing the channel and the like formed on a rear surface of the cartridge according to another embodiment.

As particularly shown in FIG. 13, similarly to the front-surface-side channel unit 24a, the rear-surface-side channel unit 24b is formed on the rear surface of the sidewall of the reservoir accommodation unit 231 in the direction orthogonal to the insertion direction in a plan view. Further, the rear-surface-side channel unit 24b has the upstream opening communicating with the downstream opening of the connection channel unit 24c and the downstream opening communicating with the upstream opening of the measurement channel 25. Moreover, the downstream opening of the front-surface-side channel unit 24a and the upstream opening of the rear-surface-side channel unit 24b configured as stated above are formed to substantially overlap in a plan view.

Figure 14:
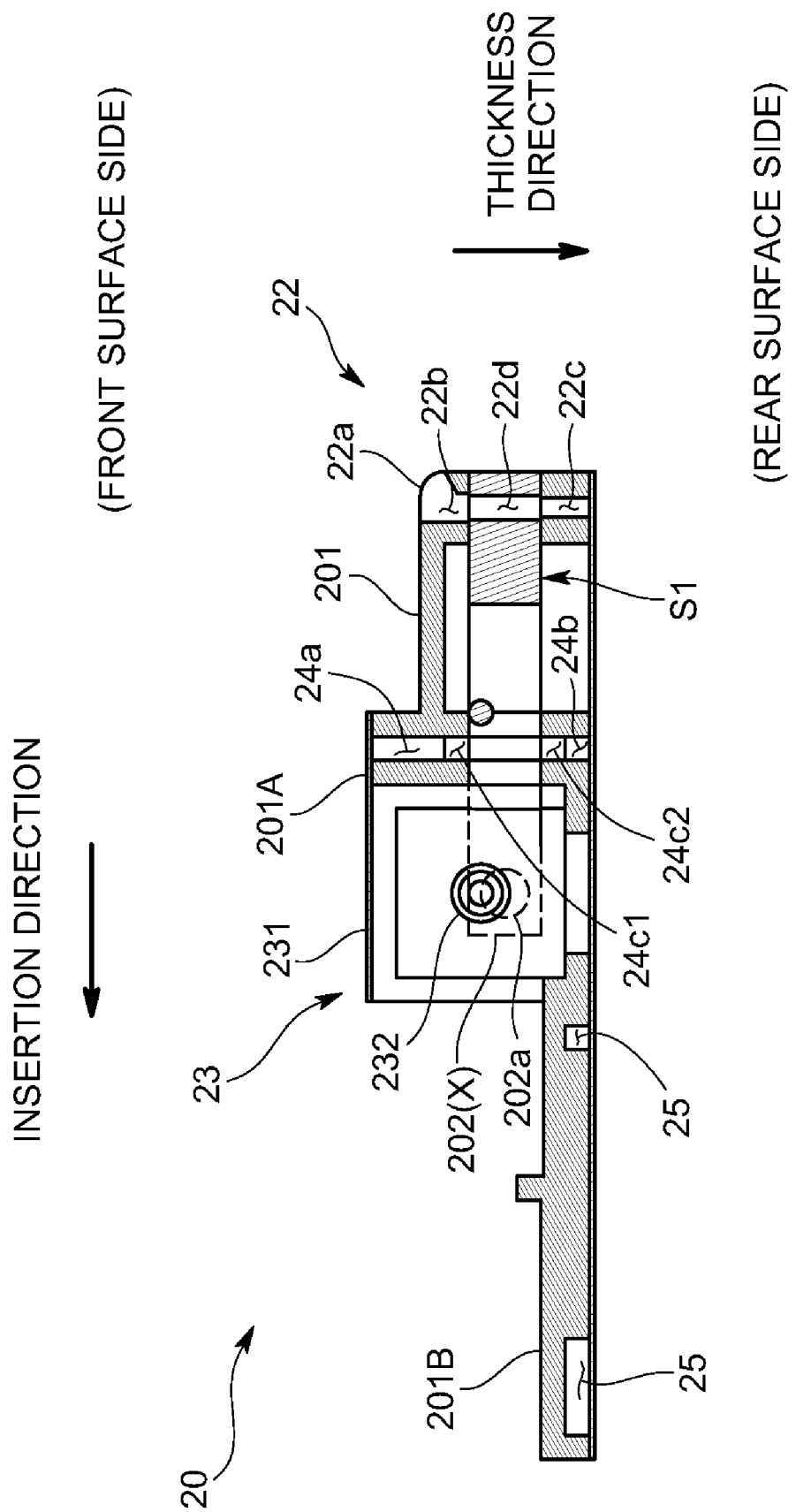
FIG. 14 is a cross-sectional view of the cartridge at the blood quantifying position, taken along a line A-A of FIG. 12 according to another embodiment.
Figure 15:
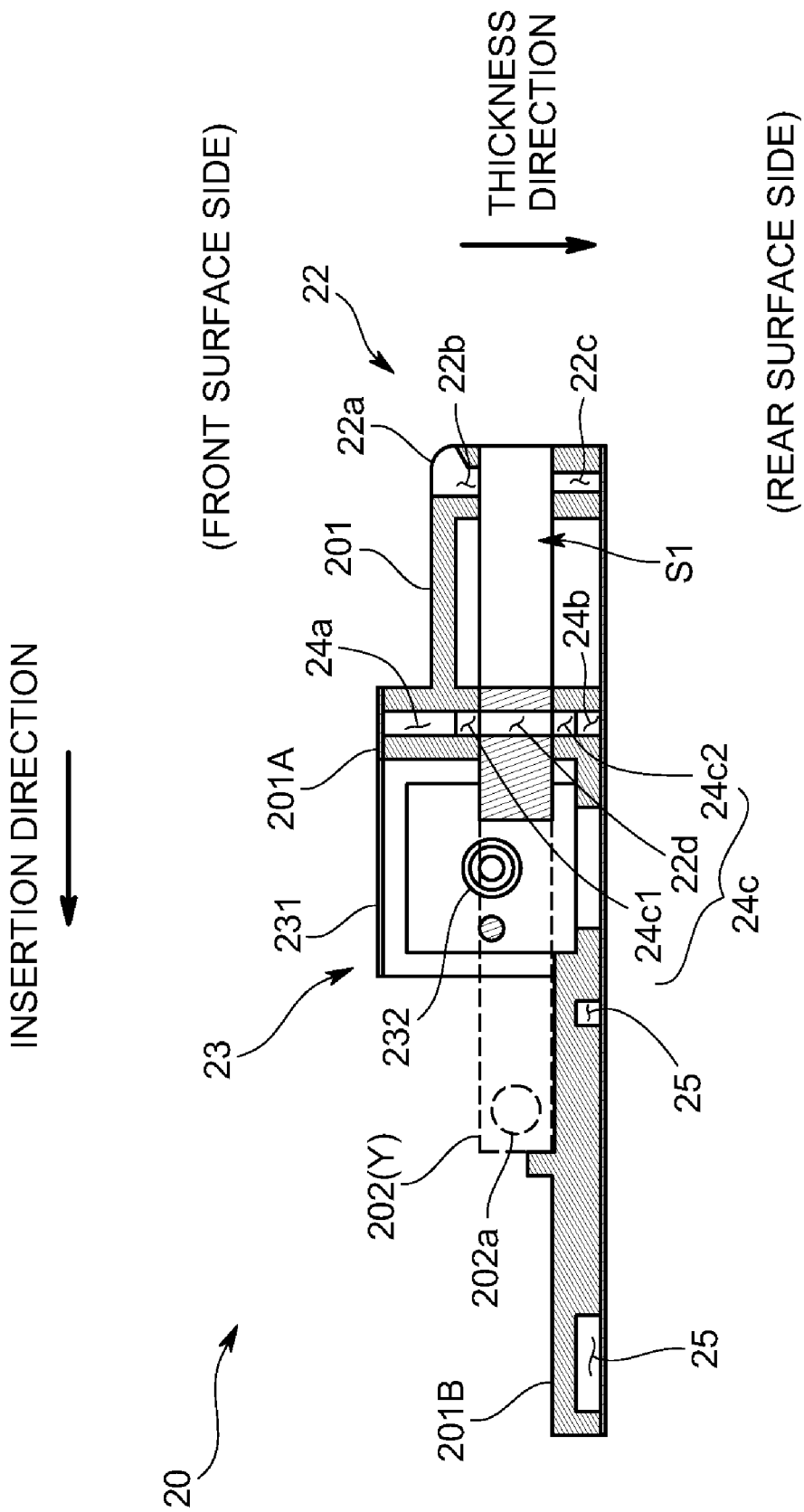
FIG. 15 is a cross-sectional view of the cartridge at the blood introduction position, taken along the line A-A of FIG. 12 according to another embodiment.
Figure 16:
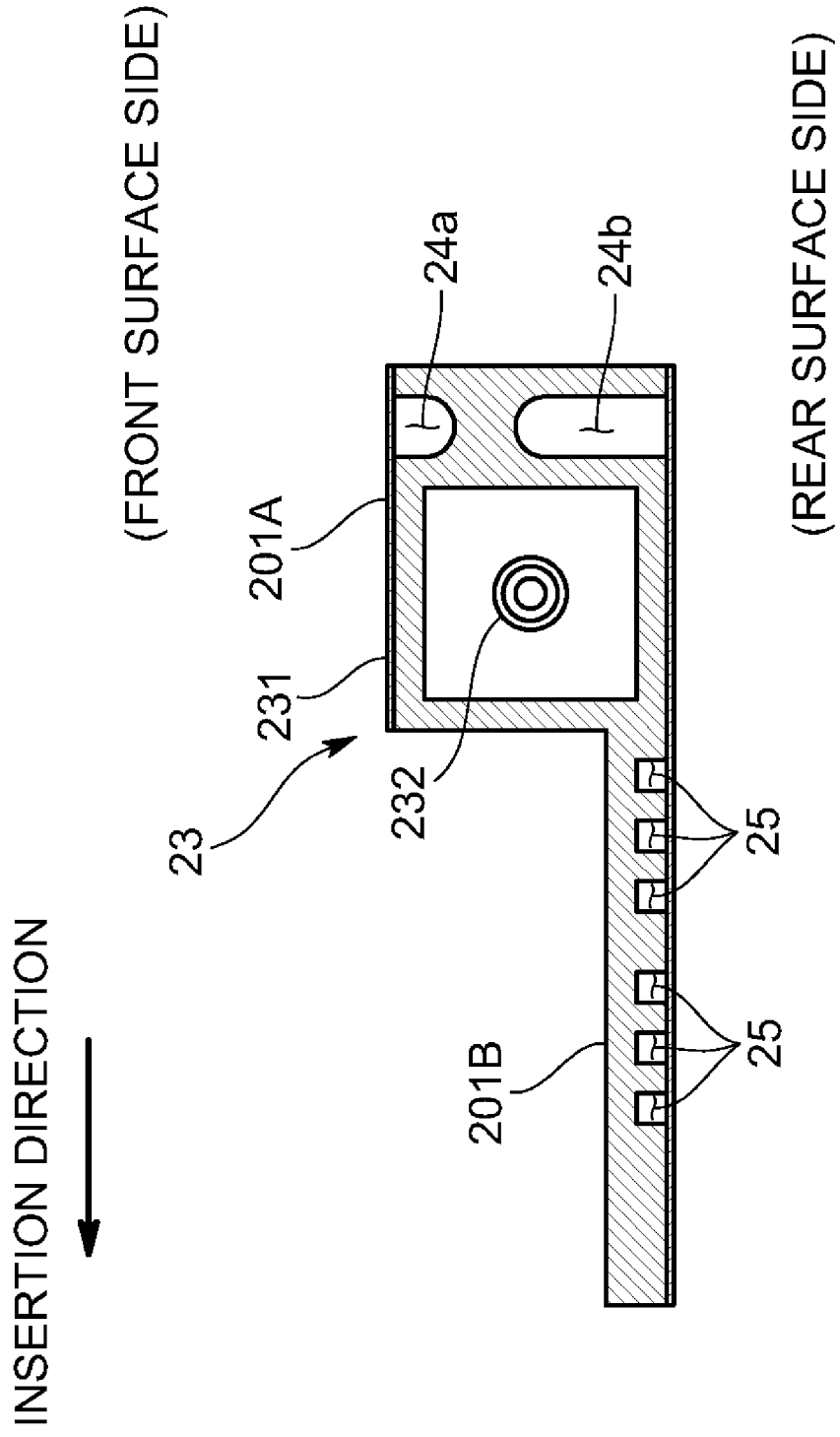
FIG. 16 is a cross-sectional view of the cartridge, taken along a line B-B of FIG. 12 according to another embodiment.

As shown in FIGS. 14, 15 and the like, the connection channel unit 24c has the upstream opening communicating with the downstream opening of the front-surface-side channel unit 24a and the downstream opening communicating with the upstream opening of the rear-surface-side channel unit 24b. The connection channel unit 24c connects the front-surface-side channel unit 24a to the rear-surface-side channel unit 24b in the thickness direction.

Specifically, the connection channel unit 24c is configured to include the front-surface-side connection channel unit 24c1 communicating with the downstream opening of the front-surface-side channel unit 24a, the rear-surface-side connection channel unit 24c2 formed opposite to the front-surface-side connection channel unit 24c1 across the space 51 (space forming the sliding path for the sliding body 202) and communicating with the upstream opening of the rear-surface-side channel unit 24b, and the quantifying capillary channel 22d of the sliding body 202 slidably provided in the space 51. The front-surface-side connection channel unit 24c1 has one end communicating with the front-surface-side channel unit 24a and the other end opening to the space 51. The rear-surface-side connection channel unit 24c2 has one end opening to the space 51 and the other end communicating with the rear-surface-side channel unit 24b.

That is, if the sliding body 202 is at the blood quantifying position X, the connection channel unit 24c is not formed. Accordingly, the front-surface-side channel unit 24a does not communicate with the rear-surface-side channel unit 24b (see FIG. 14). If the sliding body 202 is at the blood introduction position Y, the connection channel unit 24c is formed. Accordingly, the front-surface-side channel unit 24a communicates with the rear-surface-side channel unit 24b (see FIG. 15). In this way, if the sliding body 202 is at the blood introduction position Y, then the connection channel unit 24c is formed, and the quantified blood is introduced into the mixture channel 24. In this state, attraction of the reagent by the fluid supply unit 13 enables the reagent to be introduced into the front-surface-side channel unit 24a, the connection channel unit 24c, and the rear-surface-side channel unit 24b from the inner channel of the reagent-lead needle 232 inserted into the reagent reservoir 3. Further, as a result of attraction and discharge operations performed by the suction pump of the fluid supply unit 13, the quantified blood and the reagent are mixed up and the diluted blood is produced in the mixture channel 24.

As shown in FIGS. 13 to 16, the measurement channel 25 is formed on the rear surface of the plane thin portion 201B that is the measurement-channel formation portion provided continuously to the insertion-side side surface of the thick portion 201A of the cartridge main body 201. This plane thin portion 201B is formed so that the rear surface of the plane thin portion 201B is flush with that of the thick portion 201A of the cartridge main body 201. As shown in FIG. 13, the measurement channel 25 is formed to communicate with a downstream exit of the mixture channel 24 (rear-surface-side channel unit 24b of the mixture channel 24 to be specific). The measurement channel 25 is formed entirely on the rear surface of the plane thin portion 201B of the cartridge main body 201 from the downstream outlet in the insertion direction. On an upstream side of the measurement channel 25, opposing inner walls of the measurement channel 25 are made proximate to each other so as to constitute a gap of about 1 mm, and the gap forms an aperture 26. Note that a magnitude of the gap for forming the aperture 26 can be appropriately set according to the size of each measurement target cell (blood cell in the second embodiment).

Figure 17:
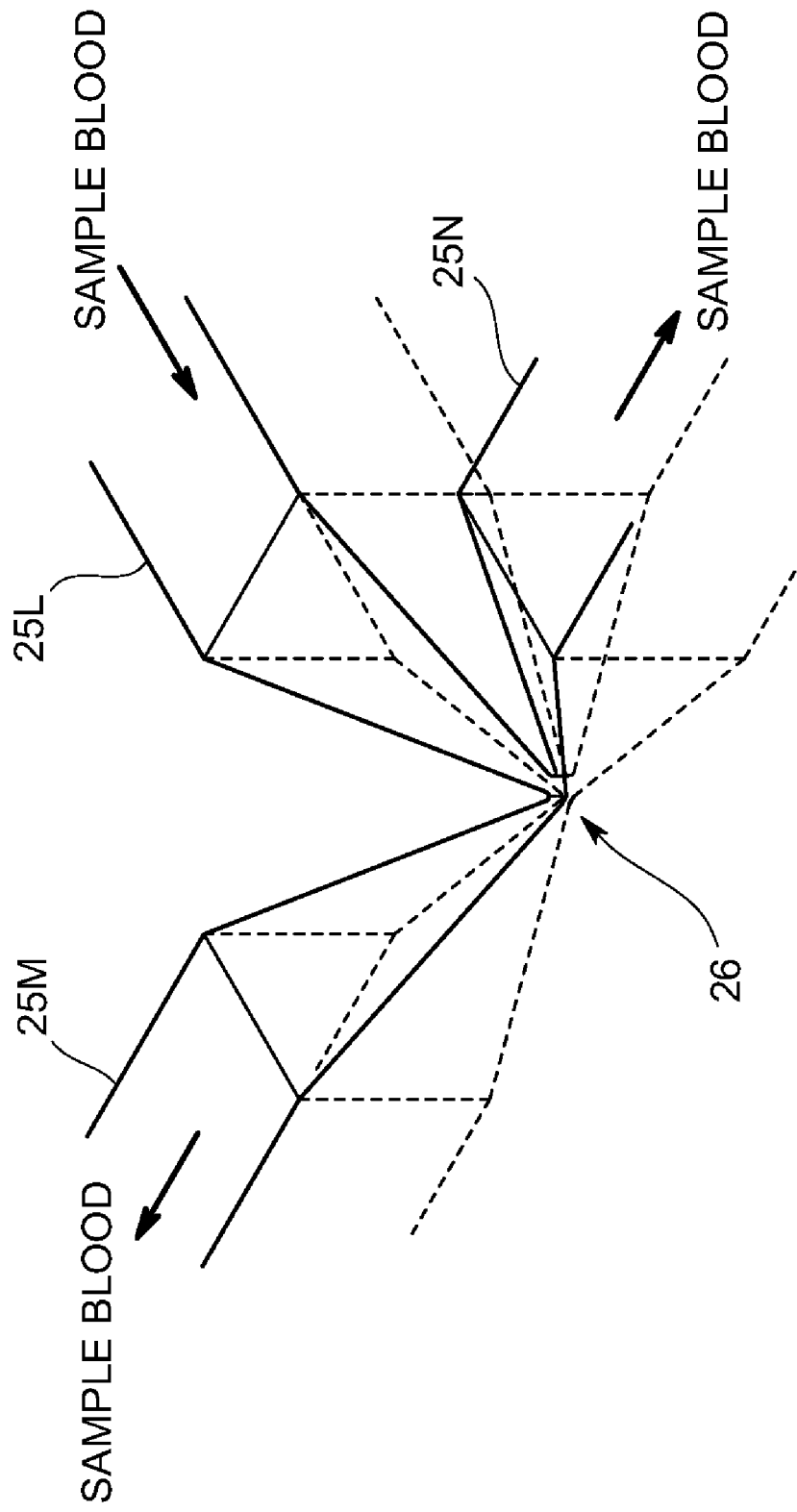
FIG. 17 is an enlarged perspective view showing the aperture according to another embodiment.

As particularly shown in FIG. 17, the measurement channel 25 branches into two channels downstream from a position at which this aperture 26 is formed. Out of branches of the measurement channel 25 near the aperture 26, a channel 25L upstream of the aperture 26 is configured so that a distance between the opposing inner walls is gradually narrower as the channel 25L is closer to the aperture 26. Each of channels 25M and 25N downstream of the aperture 26 is configured so that a distance between the opposing inner walls is gradually wider as the channel 25M or 25N is farther from the aperture 26. The other regions are almost equal in channel width. By forming the measurement channel 25 as stated above, the blood cells contained in the diluted blood pass through the aperture 26 in regular order without disturbance of flow of the diluted blood passing through the aperture 26.

A filter F for removing foreign matters of a predetermined size (for example, equal to or greater than 50 μm) contained in the diluted blood such as dust and dirt is formed upstream of the aperture 26. This filter F is formed of a plurality of cylinders arranged at predetermined intervals. By forming the filter F, no foreign matter reaches the aperture 26, so that it is possible to improve measurement precision of cell analysis.

The channels 25M and 25N downstream of the aperture 26 are described more specifically. Each of the channels 25M and 25N is formed into a meander channel constituted by a linear channel formed to traverse the insertion direction of the cartridge main body 201 from a position from which the measurement channel 25 branches off and a bent channel formed by bending the linear channel (see FIGS. 13 and 17). In this way, the measurement channel 25 is configured to be bent a plurality of times on ends in the insertion direction of the cartridge main body 201 and is formed almost on an entire surface of the cartridge main body 201. This can secure the measurement channel 25 as long as possible in a limited region in the cartridge main body 201. Furthermore, the terminal end of the measurement channel 25 communicates with the opening H open to the surface (lower surface) of the cartridge main body 201. The measurement channel 25 is whereby configured to cause the diluted blood introduced from the downstream exit (opening) of the mixture channel 24 to move forward in the measurement channel 25 so as to force out the air contained in the measurement channel 25 from the opening H.

As shown in FIG. 13, a pair of electrodes 27 (hereinafter, also "first electrodes 27") serving as detecting units is arranged across the aperture 26 at positions of branching parts of the measurement channel 25 downstream of the aperture 26 and in contact with the diluted blood passing through the aperture 26, respectively. Each of the electrodes 27 is configured to include a fluid contact unit 27a formed to face the inner wall of the measurement channel 25, a lead wire (not shown) led out from the fluid contact unit 27a, and a signal fetching unit 27b appearing on the front surface of the cartridge 20 above the notch 21 to electrically conduct to the fluid contact unit 27a via the lead wire.

Moreover, the second electrode 28 is provided downstream of the fluid contact unit 27a of each of the first electrodes 27. The second electrode 28 is configured to include a fluid detecting unit 28a provided downstream of the fluid contact unit 27a (to be specific, upstream of the terminal end of the measurement channel 25 by the predetermined distance) and detecting whether the channel capacity of the measurement channel 25 is equal to the preset constant capacity, a lead wire (not shown) led out from the fluid detecting unit 28a, and the detected-signal output unit 28b continuous to the terminal end of the lead wire and provided laterally of the signal fetching units 27b. Each of the second electrodes 28 functions as the fluid level sensor that detects that the diluted blood has arrived at the fluid detecting unit 28a.

That is, if the diluted blood flowing in the measurement channel 25 after contacting one fluid contact unit 27a contacts the fluid detecting unit 28a, then an electric signal is generated, the electric signal is transmitted to the detected-signal output unit 28b via the lead wire led out from the liquid detecting unit 28a, and arrival of the diluted blood at the predetermined arrival position in the measurement channel 25 is transmitted to the measurement-unit main body 10. If the arrival of the diluted blood at the predetermined position in the measurement channel 25 is detected, the fluid supply unit 13 stops supplying the diluted blood, thereby making it possible to prevent the diluted blood from arriving at the opening H on the terminal end of the measurement channel 25 and overflowing.

Note that the signal fetching units 27b of the first electrodes 27 and the detected-signal output units 28b of the second electrodes 28 are arranged to stand one behind another as already stated and are configured to electrically contact the conduction unit 14a of the connector 14 when the cartridge 20 is attached to the measurement-unit main body 10.

Figure 18:
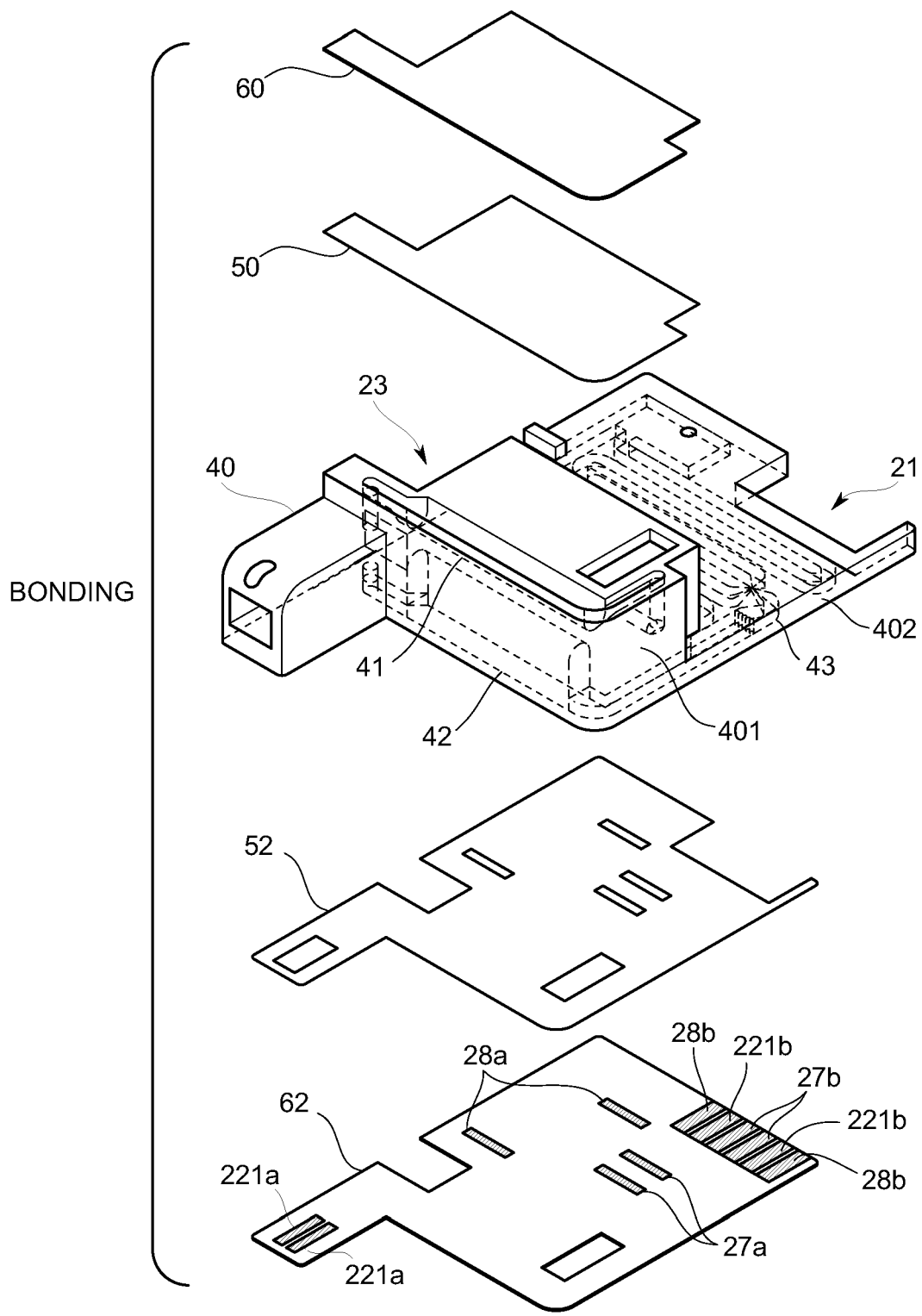
FIG. 18 is an exploded perspective view of a cartridge main body according to another embodiment.

Referring to FIG. 18, an internal configuration of the cartridge main body 201 is described in detail. As shown in FIG. 18, the cartridge main body 201 is configured to include the base material 40 made of, for example, PMMA, having first and second bottomed grooves 41 and 42 formed on front and rear surfaces of a thick portion 401, respectively, and having a third bottomed groove 43 formed on a rear surface of a thin portion 402, and first and second films 60 and 62 serving as PET cover members bonded onto the front and rear surfaces of the base material 40 via first and second adhesive sheets 50 and 52, respectively.

The first bottomed groove 41 forming the front-surface-side channel unit 24a of the mixture channel 24 is formed on the front surface of the thick portion 401 of the base material 40. The second bottomed groove 42 forming the rear-surface-side channel unit 24b of the mixture channel 24 is formed on the rear surface of the thick portion 401. The front-surface-side connection channel unit 24c1 of the connection channel unit 24c is formed on a downstream end of the first bottomed groove 41, and the rear-surface-side connection channel unit 24c2 of the connection channel unit 24c is formed on an upstream end of the second bottomed groove 42. The reservoir holder 23 is formed in the thick portion 401, and a channel connecting the inner channel of the reagent-lead needle 232 of the reservoir holder 23 to an upstream end of the first bottomed groove 41 is also formed in the thick portion 401. Further, the sliding body 202 is inserted into the space S1 formed in the thick portion 401.

The third bottomed groove 43 forming the measurement channel 25 is formed on the rear surface of the thin portion 402 of the base material 40. A start point of this third bottomed groove 43 is continuous to a terminal end of the second bottomed groove 42. As stated, the third bottomed groove 43 is gradually narrower near upstream of the position at which the aperture 26 is formed, and the third bottomed groove 43 is gradually wider near downstream of the position at which the aperture 26 is formed. Such bottomed grooves 41 to 43 and the cylinders of the filter F are formed by machining the surface of the base material 40 by an arbitrary machining method such as micromachining, hot embossing or sterolithography.

The first film 60 is formed into a shape almost identical to a surface shape of the thick portion 401 of the base material 40. The front-surface-side channel unit 24a of the mixture channel 24 is constituted by covering an opening of the first bottomed groove 41 with the first film 60 when the first film 60 is bonded onto the front surface of the thick portion 401 of the base material 40. The second film 62 is formed into a shape almost identical to surface shapes of the thick portion 401 and thin portion 402 of the base material 40. The rear-surface-side channel unit 24b of the mixture channel 24 and the measurement channel 25 are constituted by covering openings of the second bottomed groove 42 and third bottomed groove 43 with the second film 62 when the second film 62 is bonded onto the rear surface of the base material 40. In the second film 62, a through-hole 62a is formed at a position corresponding to a terminal end of the third bottomed groove 43. Furthermore, in the second film 62, a notch is not provided at a position corresponding to the notch 21 of the base material 40. The second film 62 is configured to cover an upper portion of the notch 21 with a part of the second film 62 when being bonded onto the base material 40. In an area of the second film 62 covering up the upper portion of the notch 21, the signal fetching units 27b constituting the respective first electrodes 27, the detected-signal output units 28b constituting the respective second electrodes 28, and the signal fetching unit 221b constituting the fluid sensor 221 are formed.

The first electrodes 27 and the second electrodes 28 are formed by covering silver (Ag) serving as a conductive metal applied by a trace amount onto predetermined positions on the surface of the second film 62 with a thin carbon coat (C). As stated, the fluid contact unit 27a and the fluid detecting unit 28a constituting one first electrode 27 and the corresponding second electrode 28, respectively electrically conduct to each other by contact with the diluted blood flowing in the measurement channel 25. The fluid contact unit 27a and the fluid detecting unit 28a are also electrically connected to the signal fetching unit 27b and the detected-signal output unit 28b via the lead wires, respectively. The fluid sensor 221 is formed similarly. The first electrodes 27 and the like are formed by such a method as screen printing or sputtering.

The first adhesive sheet 50 for bonding the front surface of the thick portion 401 of the base material 40 to the first film 60 is made of a thin-film solid adhesive 50 covering up the entire front surface of the thick portion 401 of the base material 40. The second adhesive sheet 52 for bonding the rear surface of the base material 40 to the second film 62 is made of a thin-film solid adhesive covering up the entire rear surface of the base material 40 except for portions corresponding to locations where the fluid contact units 27a, the fluid detecting units 28a, and the fluid contact units 221a are formed on the second film 62. The solid adhesives have the property of being solid at normal temperature but being molten to bear adhesion when being heated at about a predetermined temperature or higher. The first and second adhesive sheets 50 and 52 made of the solid adhesives are sandwiched between the base material 40 and the first and second films 60 and 62 and heated in the sandwiched state, thereby bonding the base material 40 to the first and second films 60 and 62.

[Advantageous Effects of Second Embodiment]

According to the body fluid analyzing apparatus 100 of the second embodiment configured as stated above, by configuring the mixture channel 24 to include the front-surface-side channel unit 24a, the rear-surface-side channel unit 24b, and the connection channel unit 24c, the mixture channel 24 can be formed in the thickness direction of the cartridge main body 201 and the plane size of the cartridge 20 can be made compact while making the capacity of the mixture channel 24 as large as possible. In the second embodiment, in particular, the front-surface-side channel unit 24a and the rear-surface-side channel unit 24b are formed on the sidewall of the reservoir holder 23 that corresponds to the thick portion 201A of the cartridge main body 201 in the sidewall thickness direction. This can make the capacity of the mixture channel 24 as large as possible. Furthermore, since the capacity of the mixture channel 24 can be made as large as possible, it is possible to uniformly mix up the blood that is the body fluid and the reagent that is the diluent and to thereby improve body-fluid analytical precision.

The present invention is not limited to the second embodiment.

For example, while the mixture channel is formed only on the front and rear surfaces of the reservoir holder in the second embodiment, the mixture channel can be formed to spread through the thin portion of the cartridge main body. Specifically, the rear-surface-side channel unit can be formed to spread through the thin portion of the cartridge main body. On the other hand, the measurement channel can be formed to spread through the thick portion of the cartridge main body.

Additionally, according to the second embodiment, the first-surface-side channel unit and the second-surface-side channel unit of the mixture channel are the front-surface-side channel unit and the rear-surface-side channel unit, respectively. Alternatively, the other side surface can be assumed as first or second surfaces and the first-surface-side channel unit or second-surface-side channel unit can be formed on the other side surface.

Furthermore, the second moving mechanism 73 according to the second embodiment is configured to include the bending unit utilizing the elastic deformation of the extension unit 202n of the sliding body 202. Alternatively, a hinge can be provided between the guided unit 202m of the sliding body 202 and the through-needle 71.

Moreover, while the cartridge used in the blood cell counter as the body fluid analyzer has been described in the first and second embodiments, the cartridge can be used for, for example, a protein analysis in an urine analysis or a saliva analysis.

Needless to say, the present invention is not limited to the embodiments but can be changed and modified variously in the range without departure from the spirit and scope of the invention as set forth in the Claims that follow.

REFERENCE CHARACTERS LIST

100 Body fluid analyzing apparatus
20 Cartridge (cell analysis cartridge)
201 Cartridge main body
25 Measurement channel
25a Front-surface-side channel unit
25b Rear-surface-side channel unit
25c Connection channel unit
26 Aperture
27 Detecting unit
27a Fluid contact unit
261 Aperture formation member

The invention claimed is:
1. A cell analysis cartridge comprising:
a measurement channel circulating a measurement target fluid containing cells;
an aperture provided on the measurement channel; and
a pair of electrodes, fluid contact units being arranged at positions of the electrodes across the aperture, respectively, the cell analysis cartridge performing a cell analy- sis based on an impedance change between the electrodes caused by passing of the cells through the aperture, wherein the measurement channel includes:
- a first-surface-side channel unit provided on a first surface of a cartridge main body;
- a second-surface-side channel unit provided on a second surface of the cartridge main body; and
- a connection channel unit connecting the first-surface-side channel unit to the second-surface-side channel unit, and wherein the aperture is formed in the connection channel unit, the fluid contact unit of one of the electrodes is arranged in the first-surface-side channel unit, and the fluid contact unit of other electrode is arranged in the second-surface-side channel unit.

2. The cell analysis cartridge according to claim 1, wherein the aperture is formed by narrowing a channel cross-sectional area of the connection channel unit.

3. The cell analysis cartridge according to claim 1, wherein the aperture is formed by an aperture formation member provided in a first-surface-side opening or a second-surface-side opening of the connection channel unit.

* * * * *